(12) United States Patent
Pease et al.

(10) Patent No.: US 9,642,415 B2
(45) Date of Patent: May 9, 2017

(54) SYSTEMS AND METHODS FOR MONITORING ATHLETIC PERFORMANCE

(75) Inventors: Ethan Pease, Concord, MA (US); Klaus Renner, Hollis, NH (US); Gordon Row, Groton, MA (US); Kim B. Blair, Arlington, MA (US); Christopher J. Wawrousek, Somerville, MA (US); Sean B. Murphy, North Andover, MA (US); Jean-Francois Fullum, North Reading, MA (US); Katherine Petrecca, Waltham, MA (US); Trampas Tenbroek, North Andover, MA (US)

(73) Assignee: New Balance Athletics, Inc., Boston, MA (US)

( * ) Notice: Subject to any disclaimer, the term of this patent is extended or adjusted under 35 U.S.C. 154(b) by 587 days.

(21) Appl. No.: 13/368,084

(22) Filed: Feb. 7, 2012

(65) Prior Publication Data

US 2013/0041617 A1    Feb. 14, 2013

Related U.S. Application Data

(60) Provisional application No. 61/440,243, filed on Feb. 7, 2011.

(51) Int. Cl.
  *A43B 3/00* (2006.01)
  *A63B 24/00* (2006.01)
  *G01C 22/00* (2006.01)

(52) U.S. Cl.
  CPC .......... *A43B 3/0005* (2013.01); *A43B 3/0031* (2013.01); *A63B 24/0062* (2013.01);
  (Continued)

(58) Field of Classification Search
  CPC ............ A61B 2562/0219; A61B 5/112; A61B 5/1122; A61B 5/6807; A61B 5/6828;
  (Continued)

(56) References Cited

U.S. PATENT DOCUMENTS 3,878,641 A    4/1975 Noble
4,144,769 A    3/1979 Mayer
(Continued)

FOREIGN PATENT DOCUMENTS

EP    1707065    10/2006
FR    2646545    11/1990
(Continued)

OTHER PUBLICATIONS

Pappas et al., A Reliable Gait Phase Detection System, IEEE Transactions on Neural Systems and Rehabilitation Engineering, vol. 9, No. 2, Jun. 2001.*

(Continued)

*Primary Examiner* — Gregory J Toatley
*Assistant Examiner* — Kyle R Quigley
(74) *Attorney, Agent, or Firm* — Goodwin Procter LLP

(57) ABSTRACT

The invention relates to devices and methods for monitoring one or more athletic performance characteristic of a user. An example apparatus includes a sensing unit adapted to be attachable to a shoe of a user, the sensing unit including a first sensor adapted to monitor an movement of a foot of the user while the user is in motion, the first sensor comprising a gyroscopic sensor, processing means for determining a first performance characteristic of the user based upon an output from the first sensor, the first performance characteristic comprising a foot strike location of a foot of the user upon striking a ground surface, and transmitting means for transmitting a data package representative of the performance characteristic to a remote receiver.

36 Claims, 17 Drawing Sheets

(52) U.S. Cl.
CPC ........ *G01C 22/006* (2013.01); *A63B 2220/12* (2013.01); *A63B 2220/13* (2013.01); *A63B 2220/34* (2013.01); *A63B 2220/40* (2013.01); *A63B 2220/56* (2013.01); *A63B 2220/72* (2013.01); *A63B 2230/06* (2013.01)

(58) Field of Classification Search
CPC ........ A63B 2220/803; A63B 2220/836; A63B 24/0006; A63B 24/0062
See application file for complete search history.

(56) References Cited

U.S. PATENT DOCUMENTS

| | | | |
|---|---|---|---|
| 4,216,416 A | 8/1980 | Grace | |
| 4,250,627 A | 2/1981 | Jaervenpaeae et al. | |
| 4,387,437 A | 6/1983 | Lowrey et al. | |
| 4,403,869 A | 9/1983 | Crutcher | |
| 4,487,208 A | 12/1984 | Kamens | |
| 4,499,394 A | 2/1985 | Koal | |
| 4,510,704 A | 4/1985 | Johnson | |
| 4,536,975 A | 8/1985 | Harrell | |
| 4,601,106 A | 7/1986 | Leinonen | |
| 4,630,383 A | 12/1986 | Gamm | |
| 4,741,001 A | 4/1988 | Ma | |
| 4,771,394 A * | 9/1988 | Cavanagh | A43B 3/0005 235/105 |
| 4,780,864 A | 10/1988 | Houlihan | |
| 4,793,666 A | 12/1988 | Torrence | |
| 4,814,661 A | 3/1989 | Ratzlaff et al. | |
| 4,876,500 A | 10/1989 | Wu | |
| 4,932,914 A | 6/1990 | Aranda | |
| 5,063,690 A | 11/1991 | Slenker | |
| 5,117,444 A | 5/1992 | Sutton et al. | |
| 5,323,650 A | 6/1994 | Fullen et al. | |
| 5,456,032 A | 10/1995 | Matsumoto et al. | |
| 5,456,262 A | 10/1995 | Birnbaum | |
| 5,471,405 A | 11/1995 | Marsh | |
| 5,500,635 A | 3/1996 | Mott | |
| 5,511,561 A | 4/1996 | Wanderman et al. | |
| 5,524,101 A | 6/1996 | Thorgersen et al. | |
| 5,560,114 A | 10/1996 | Laehteenmaeki | |
| 5,600,611 A | 2/1997 | Kamens | |
| 5,619,186 A | 4/1997 | Schmidt et al. | |
| 5,636,146 A | 6/1997 | Flentov et al. | |
| 5,654,718 A | 8/1997 | Beason et al. | |
| 5,663,871 A | 9/1997 | Bayani | |
| 5,678,448 A | 10/1997 | Fullen et al. | |
| 5,775,011 A | 7/1998 | Reitano, Jr. | |
| 5,810,722 A | 9/1998 | Heikkilae | |
| 5,845,235 A | 12/1998 | Luukkanen et al. | |
| 5,850,626 A | 12/1998 | Kallio | |
| 5,922,058 A | 7/1999 | Fishman et al. | |
| 5,945,911 A | 8/1999 | Healy et al. | |
| 5,955,667 A | 9/1999 | Fyfe | |
| 5,960,380 A | 9/1999 | Flentov et al. | |
| 6,018,705 A | 1/2000 | Gaudet et al. | |
| 6,029,515 A | 2/2000 | Laehteenmaki et al. | |
| 6,032,530 A | 3/2000 | Hock | |
| 6,039,446 A | 3/2000 | Lahteenmaki et al. | |
| 6,052,654 A | 4/2000 | Gaudet et al. | |
| 6,104,947 A | 8/2000 | Heikkilae et al. | |
| 6,122,340 A | 9/2000 | Darley et al. | |
| 6,159,130 A | 12/2000 | Torvinen | |
| 6,229,454 B1 | 5/2001 | Heikkilae et al. | |
| 6,240,647 B1 | 6/2001 | Moustgaard et al. | |
| 6,266,623 B1 | 7/2001 | Vock et al. | |
| 6,289,747 B1 | 9/2001 | Billen et al. | |
| 6,298,314 B1 | 10/2001 | Blackadar et al. | |
| 6,301,964 B1 | 10/2001 | Fyfe et al. | |
| 6,330,149 B1 | 12/2001 | Burrell | |
| 6,336,365 B1 | 1/2002 | Blackadar et al. | |
| 6,357,147 B1 | 3/2002 | Darley et al. | |
| 6,411,841 B2 | 6/2002 | Heikkil | |
| 6,418,181 B1 | 7/2002 | Nissil | |
| 6,434,485 B1 | 8/2002 | Beason et al. | |
| 6,493,652 B1 | 12/2002 | Ohlenbusch et al. | |
| 6,496,787 B1 | 12/2002 | Flentov et al. | |
| 6,498,994 B2 | 12/2002 | Vock et al. | |
| 6,499,000 B2 | 12/2002 | Flentov et al. | |
| 6,516,284 B2 | 2/2003 | Flentov et al. | |
| 6,529,827 B1 | 3/2003 | Beason et al. | |
| 6,536,139 B2 | 3/2003 | Darley et al. | |
| 6,537,227 B2 | 3/2003 | Kinnunen et al. | |
| 6,539,336 B1 | 3/2003 | Vock et al. | |
| 6,549,850 B2 | 4/2003 | Punkka et al. | |
| 6,551,252 B2 | 4/2003 | Sackner et al. | |
| 6,560,903 B1 | 5/2003 | Darley | |
| 6,611,789 B1 | 8/2003 | Darley | |
| 6,614,726 B2 | 9/2003 | Yamasaki et al. | |
| 6,650,282 B2 | 11/2003 | Martikka | |
| 6,679,405 B2 | 1/2004 | Zalis-Hecker et al. | |
| 6,735,542 B1 | 5/2004 | Burgett et al. | |
| 6,745,069 B2 | 6/2004 | Nissilae et al. | |
| 6,745,115 B1 | 6/2004 | Chen et al. | |
| 6,768,449 B1 | 7/2004 | Burgett et al. | |
| 6,768,450 B1 | 7/2004 | Walters et al. | |
| 6,798,378 B1 | 9/2004 | Walters et al. | |
| 6,799,114 B2 | 9/2004 | Etnyre | |
| 6,801,855 B1 | 10/2004 | Walters et al. | |
| 6,803,860 B1 | 10/2004 | Langner et al. | |
| 6,810,322 B2 | 10/2004 | Lai | |
| 6,819,549 B1 | 11/2004 | Lammers-Meis et al. | |
| 6,832,138 B1 | 12/2004 | Straub et al. | |
| 6,833,851 B1 | 12/2004 | Brunk | |
| 6,836,744 B1 | 12/2004 | Asphahani et al. | |
| 6,837,827 B1 | 1/2005 | Lee et al. | |
| 6,841,947 B2 | 1/2005 | Berg-johansen | |
| 6,856,934 B2 | 2/2005 | Vock et al. | |
| 6,862,525 B1 | 3/2005 | Beason et al. | |
| 6,865,453 B1 | 3/2005 | Burch et al. | |
| 6,876,947 B1 | 4/2005 | Darley et al. | |
| 6,882,955 B1 | 4/2005 | Ohlenbusch et al. | |
| 6,885,971 B2 | 4/2005 | Vock et al. | |
| D504,627 S | 5/2005 | Harju | |
| 6,898,550 B1 | 5/2005 | Blackadar et al. | |
| 6,958,045 B2 | 10/2005 | Takiguchi et al. | |
| 6,959,259 B2 | 10/2005 | Vock et al. | |
| 6,963,818 B2 | 11/2005 | Flentov et al. | |
| 6,967,616 B2 | 11/2005 | Etnyre | |
| 6,970,795 B1 | 11/2005 | Burgett et al. | |
| 6,978,684 B2 | 12/2005 | Nurse | |
| D514,461 S | 2/2006 | Harju | |
| 7,013,216 B2 | 3/2006 | Walters et al. | |
| 7,034,747 B1 | 4/2006 | Walters et al. | |
| 7,043,355 B2 | 5/2006 | Lai | |
| 7,047,113 B1 | 5/2006 | Burch et al. | |
| 7,054,725 B2 | 5/2006 | Burch et al. | |
| 7,054,784 B2 | 5/2006 | Flentov et al. | |
| 7,057,551 B1 | 6/2006 | Vogt | |
| 7,072,246 B2 | 7/2006 | Lizzi | |
| 7,072,789 B2 | 7/2006 | Vock et al. | |
| 7,085,678 B1 | 8/2006 | Burrell et al. | |
| 7,092,846 B2 | 8/2006 | Vock et al. | |
| 7,113,450 B2 | 9/2006 | Plancon et al. | |
| 7,129,835 B2 | 10/2006 | Nikkola | |
| 7,142,152 B2 | 11/2006 | Burgett et al. | |
| 7,146,686 B2 | 12/2006 | Saaski et al. | |
| 7,152,286 B2 | 12/2006 | Rooney et al. | |
| 7,152,470 B2 | 12/2006 | Impio et al. | |
| 7,158,912 B2 | 1/2007 | Vock et al. | |
| 7,162,392 B2 | 1/2007 | Vock et al. | |
| 7,171,331 B2 | 1/2007 | Vock et al. | |
| 7,174,277 B2 | 2/2007 | Vock et al. | |
| 7,187,924 B2 | 3/2007 | Ohlenbusch et al. | |
| 7,188,439 B2 | 3/2007 | DiBenedetto et al. | |
| 7,191,644 B2 | 3/2007 | Haselhurst et al. | |
| 7,200,517 B2 | 4/2007 | Darley et al. | |
| 7,215,279 B1 | 5/2007 | Poindexter et al. | |
| 7,215,601 B2 | 5/2007 | Plancon et al. | |
| 7,225,565 B2 | 6/2007 | DiBenedetto et al. | |
| 7,234,348 B2 | 6/2007 | Spampinato et al. | |
| 7,245,254 B1 | 7/2007 | Vogt | |
| 7,271,774 B2 | 9/2007 | Puuri | |
| 7,292,867 B2 | 11/2007 | Werner et al. | |

(56) References Cited

U.S. PATENT DOCUMENTS

| | | |
|---|---|---|
| 7,324,002 B2 | 1/2008 | Iso-Heiko et al. |
| 7,349,805 B2 | 3/2008 | Kaltto et al. |
| 7,353,136 B2 | 4/2008 | Vock et al. |
| 7,353,137 B2 | 4/2008 | Vock et al. |
| 7,353,139 B1 | 4/2008 | Burrell et al. |
| 7,363,121 B1 | 4/2008 | Chen et al. |
| 7,363,521 B1 | 4/2008 | Mehan |
| 7,377,180 B2 | 5/2008 | Cunningham |
| 7,379,712 B2 | 5/2008 | Saarnimo |
| 7,382,285 B2 | 6/2008 | Horvath et al. |
| 7,383,081 B2 | 6/2008 | Butt et al. |
| 7,386,373 B1 | 6/2008 | Chen et al. |
| 7,386,401 B2 | 6/2008 | Vock et al. |
| 7,387,029 B2 | 6/2008 | Cunningham |
| 7,398,151 B1 | 7/2008 | Burrell et al. |
| 7,428,471 B2 | 9/2008 | Darley et al. |
| 7,428,472 B2 | 9/2008 | Darley et al. |
| 7,429,948 B2 | 9/2008 | Burgett et al. |
| 7,433,805 B2 | 10/2008 | Vock et al. |
| 7,437,268 B1 * | 10/2008 | Pathak .............. G06Q 10/063 702/182 |
| 7,451,056 B2 | 11/2008 | Flentov et al. |
| 7,457,724 B2 | 11/2008 | Vock et al. |
| 7,466,979 B2 | 12/2008 | Ohlenbusch et al. |
| 7,467,060 B2 | 12/2008 | Kulach et al. |
| 7,468,692 B1 | 12/2008 | Wiegers |
| 7,480,512 B2 | 1/2009 | Graham et al. |
| 7,483,789 B1 | 1/2009 | Walters et al. |
| 7,484,320 B2 | 2/2009 | Butt et al. |
| 7,489,241 B2 | 2/2009 | Miettinen et al. |
| 7,506,460 B2 | 3/2009 | DiBenedetto et al. |
| 7,512,515 B2 | 3/2009 | Vock et al. |
| 7,512,793 B1 | 3/2009 | Harris |
| 7,515,938 B2 | 4/2009 | Ruotsalainen et al. |
| 7,526,840 B2 | 5/2009 | Pernu et al. |
| 7,526,954 B2 | 5/2009 | Haselhurst et al. |
| 7,534,206 B1 | 5/2009 | Lovitt et al. |
| 7,552,031 B2 | 6/2009 | Vock et al. |
| 7,559,127 B2 | 7/2009 | Rooney et al. |
| 7,566,290 B2 | 7/2009 | Lee et al. |
| 7,587,937 B2 | 9/2009 | Haselhurst et al. |
| 7,596,891 B2 | 10/2009 | Carnes et al. |
| 7,600,426 B2 | 10/2009 | Savolainen et al. |
| 7,600,430 B2 | 10/2009 | Palin et al. |
| 7,601,098 B1 | 10/2009 | Lee et al. |
| 7,602,302 B2 | 10/2009 | Hokuf et al. |
| 7,607,243 B2 | 10/2009 | Berner, Jr. et al. |
| 7,613,356 B2 | 11/2009 | Uchiyama et al. |
| 7,617,071 B2 | 11/2009 | Darley et al. |
| 7,620,520 B2 | 11/2009 | Vock et al. |
| 7,623,078 B2 | 11/2009 | Wang |
| 7,623,987 B2 | 11/2009 | Vock et al. |
| 7,625,314 B2 | 12/2009 | Ungari et al. |
| 7,627,451 B2 | 12/2009 | Vock et al. |
| 7,631,382 B2 | 12/2009 | DiBenedetto et al. |
| 7,637,747 B2 | 12/2009 | Jaatinen et al. |
| 7,640,135 B2 | 12/2009 | Vock et al. |
| 7,658,694 B2 | 2/2010 | Ungari |
| 7,662,064 B2 | 2/2010 | Lee et al. |
| 7,667,641 B1 | 2/2010 | Poindexter et al. |
| 7,670,295 B2 | 3/2010 | Sackner et al. |
| 7,671,581 B2 | 3/2010 | Noenen |
| 7,676,960 B2 | 3/2010 | DiBenedetto et al. |
| 7,676,961 B2 | 3/2010 | DiBenedetto et al. |
| 7,693,668 B2 | 4/2010 | Vock et al. |
| 7,696,904 B2 | 4/2010 | Horvath et al. |
| 7,698,058 B2 | 4/2010 | Chen et al. |
| 7,698,101 B2 | 4/2010 | Alten et al. |
| 7,706,815 B2 | 4/2010 | Graham et al. |
| 7,726,206 B2 | 6/2010 | Terrafranca, Jr. et al. |
| 7,728,723 B2 | 6/2010 | Niva et al. |
| 7,736,242 B2 | 6/2010 | Stites et al. |
| 7,740,551 B2 | 6/2010 | Nurnberg et al. |
| 7,752,011 B2 | 7/2010 | Niva et al. |
| 7,758,523 B2 | 7/2010 | Collings et al. |
| 7,764,990 B2 | 7/2010 | Martikka et al. |
| 7,768,415 B2 | 8/2010 | Blackadar |
| 7,771,320 B2 | 8/2010 | Riley et al. |
| 7,771,371 B2 | 8/2010 | Avni |
| 7,778,118 B2 | 8/2010 | Lyons et al. |
| 7,787,857 B2 | 8/2010 | Peterman |
| 7,789,802 B2 | 9/2010 | Lee et al. |
| 7,795,523 B2 | 9/2010 | Lumme et al. |
| 7,797,039 B2 | 9/2010 | Koivumaa et al. |
| 7,803,117 B2 | 9/2010 | Martikka et al. |
| 7,805,149 B2 | 9/2010 | Werner et al. |
| 7,805,150 B2 | 9/2010 | Graham et al. |
| 7,813,887 B2 | 10/2010 | Vock et al. |
| 7,821,878 B2 | 10/2010 | Plancon et al. |
| 7,822,546 B2 | 10/2010 | Lee |
| 7,827,000 B2 | 11/2010 | Stirling et al. |
| 7,828,697 B1 | 11/2010 | Oberrieder et al. |
| 7,840,378 B2 | 11/2010 | Vock et al. |
| 7,856,339 B2 | 12/2010 | Vock et al. |
| 7,860,666 B2 | 12/2010 | Vock et al. |
| 7,878,055 B2 | 2/2011 | Balzano |
| 7,878,945 B2 | 2/2011 | Ungari et al. |
| 7,878,979 B2 | 2/2011 | Derchak |
| 7,887,459 B2 | 2/2011 | Ungari et al. |
| 7,889,085 B2 | 2/2011 | Downey et al. |
| 7,901,326 B2 | 3/2011 | Niva et al. |
| 7,905,026 B2 | 3/2011 | Martikka et al. |
| 7,911,339 B2 | 3/2011 | Vock et al. |
| 7,914,418 B2 | 3/2011 | Nissila |
| 7,917,198 B2 | 3/2011 | Ahola et al. |
| 7,918,811 B2 | 4/2011 | Lussier et al. |
| 7,921,716 B2 | 4/2011 | Morris Bamberg et al. |
| 7,936,226 B2 | 5/2011 | Akkila |
| 7,941,160 B2 | 5/2011 | Werner et al. |
| 7,949,488 B2 | 5/2011 | Flentov et al. |
| 7,953,549 B2 | 5/2011 | Graham et al. |
| 7,957,752 B2 | 6/2011 | Werner et al. |
| 7,961,151 B2 | 6/2011 | Wang et al. |
| 7,962,312 B2 | 6/2011 | Darley et al. |
| 7,966,154 B2 | 6/2011 | Vock et al. |
| 7,980,009 B2 | 7/2011 | Carnes et al. |
| 7,994,931 B2 | 8/2011 | Karstens et al. |
| 7,997,007 B2 | 8/2011 | Sanabria-Hernandez |
| 8,011,242 B2 | 9/2011 | O'Neill et al. |
| 8,036,850 B2 | 10/2011 | Kulach et al. |
| 8,036,851 B2 | 10/2011 | Vock et al. |
| 8,055,469 B2 | 11/2011 | Kulach et al. |
| 8,060,337 B2 | 11/2011 | Kulach et al. |
| 8,126,675 B2 | 2/2012 | Vock et al. |
| 2003/0163287 A1 | 8/2003 | Vock et al. |
| 2003/0197597 A1 * | 10/2003 | Bahl et al. .................. 340/7.58 |
| 2003/0224337 A1 | 12/2003 | Shum et al. |
| 2004/0173220 A1 | 9/2004 | Harry et al. |
| 2005/0010139 A1 | 1/2005 | Aminian et al. |
| 2005/0126370 A1 * | 6/2005 | Takai et al. .................... 84/636 |
| 2005/0177059 A1 | 8/2005 | Koivumaa et al. |
| 2006/0004294 A1 | 1/2006 | Juntunen et al. |
| 2006/0031039 A1 | 2/2006 | Flentov et al. |
| 2006/0183990 A1 | 8/2006 | Tolvanen |
| 2007/0006489 A1 | 1/2007 | Case, Jr. et al. |
| 2007/0010341 A1 | 1/2007 | Miettinen et al. |
| 2007/0159926 A1 | 7/2007 | Prstojevich et al. |
| 2007/0173903 A1 | 7/2007 | Goren et al. |
| 2007/0247306 A1 | 10/2007 | Case, Jr. |
| 2007/0250286 A1 | 10/2007 | Duncan et al. |
| 2007/0260421 A1 | 11/2007 | Berner et al. |
| 2007/0285868 A1 | 12/2007 | Lindberg et al. |
| 2007/0288984 A1 | 12/2007 | Kim |
| 2008/0053253 A1 | 3/2008 | Moore et al. |
| 2008/0096726 A1 | 4/2008 | Riley et al. |
| 2008/0119329 A1 | 5/2008 | Punkka et al. |
| 2008/0125288 A1 | 5/2008 | Case |
| 2008/0200310 A1 | 8/2008 | Tagliabue |
| 2008/0214360 A1 | 9/2008 | Stirling et al. |
| 2008/0258921 A1 * | 10/2008 | Woo et al. .................. 340/573.1 |
| 2008/0319330 A1 | 12/2008 | Juntunen et al. |
| 2009/0048044 A1 | 2/2009 | Oleson et al. |
| 2009/0113762 A1 | 5/2009 | Leimer et al. |
| 2009/0144639 A1 | 6/2009 | Nims et al. |

(56) References Cited

U.S. PATENT DOCUMENTS

| | | |
|---|---|---|
| 2009/0163322 A1 | 6/2009 | Andren et al. |
| 2009/0212941 A1 | 8/2009 | Vock et al. |
| 2009/0233771 A1 | 9/2009 | Quatrochi et al. |
| 2009/0258710 A1 | 10/2009 | Quatrochi et al. |
| 2009/0265958 A1 | 10/2009 | DiBenedetto et al. |
| 2009/0270744 A1 | 10/2009 | Prstojevich et al. |
| 2009/0272007 A1 | 11/2009 | Beers et al. |
| 2009/0284368 A1 | 11/2009 | Case, Jr. |
| 2009/0312657 A1 | 12/2009 | Martikka et al. |
| 2010/0035724 A1 | 2/2010 | Ungari et al. |
| 2010/0036639 A1 | 2/2010 | Vock et al. |
| 2010/0037489 A1 | 2/2010 | Berner, Jr. et al. |
| 2010/0041517 A1 | 2/2010 | Ungari et al. |
| 2010/0042182 A1 | 2/2010 | Chan et al. |
| 2010/0042427 A1 | 2/2010 | Graham et al. |
| 2010/0050478 A1 | 3/2010 | DiBenedetto et al. |
| 2010/0057398 A1 | 3/2010 | Darley et al. |
| 2010/0063778 A1 | 3/2010 | Schrock et al. |
| 2010/0063779 A1 | 3/2010 | Schrock et al. |
| 2010/0076692 A1 | 3/2010 | Vock et al. |
| 2010/0130123 A1 | 5/2010 | Lindman |
| 2010/0130315 A1 | 5/2010 | Steidle |
| 2010/0151996 A1 | 6/2010 | Alten et al. |
| 2010/0170337 A1 | 7/2010 | Ahlstrom |
| 2010/0184563 A1 | 7/2010 | Molyneux et al. |
| 2010/0184564 A1 | 7/2010 | Molyneux et al. |
| 2010/0185398 A1 | 7/2010 | Berns et al. |
| 2010/0187074 A1 | 7/2010 | Manni |
| 2010/0197403 A1 | 8/2010 | Niva et al. |
| 2010/0211355 A1 | 8/2010 | Horst et al. |
| 2010/0216563 A1 | 8/2010 | Stites et al. |
| 2010/0216564 A1 | 8/2010 | Stites et al. |
| 2010/0216565 A1 | 8/2010 | Stites et al. |
| 2010/0228134 A1 | 9/2010 | Martikka et al. |
| 2010/0248852 A1 | 9/2010 | Lee |
| 2010/0250208 A1 | 9/2010 | Leskela et al. |
| 2010/0273434 A1 | 10/2010 | Blackadar |
| 2010/0279824 A1 | 11/2010 | Chapa, Jr. et al. |
| 2010/0279825 A1 | 11/2010 | Riley et al. |
| 2010/0292050 A1 | 11/2010 | DiBenedetto et al. |
| 2010/0292598 A1 | 11/2010 | Roschk et al. |
| 2010/0292599 A1 | 11/2010 | Oleson et al. |
| 2010/0292600 A1 | 11/2010 | DiBenedetto et al. |
| 2010/0305480 A1* | 12/2010 | Fu et al. ............ 600/595 |
| 2010/0311544 A1 | 12/2010 | Robinette et al. |
| 2010/0332188 A1 | 12/2010 | Vock et al. |
| 2011/0003665 A1 | 1/2011 | Burton et al. |
| 2011/0009777 A1 | 1/2011 | Reichow et al. |
| 2011/0022357 A1 | 1/2011 | Vock et al. |
| 2011/0032105 A1 | 2/2011 | Hoffman et al. |
| 2011/0054270 A1 | 3/2011 | Derchak |
| 2011/0054271 A1 | 3/2011 | Derchak et al. |
| 2011/0054272 A1 | 3/2011 | Derchak |
| 2011/0054289 A1 | 3/2011 | Derchak et al. |
| 2011/0054290 A1 | 3/2011 | Derchak et al. |
| 2011/0054358 A1 | 3/2011 | Kim et al. |
| 2011/0054359 A1 | 3/2011 | Sazonov et al. |
| 2011/0060550 A1 | 3/2011 | Vock et al. |
| 2011/0069589 A1 | 3/2011 | Plancon et al. |
| 2011/0077904 A1 | 3/2011 | Jung et al. |
| 2011/0082394 A1 | 4/2011 | Chiu et al. |
| 2011/0082641 A1 | 4/2011 | Werner et al. |
| 2011/0087115 A1 | 4/2011 | Sackner et al. |
| 2011/0105861 A1 | 5/2011 | Derchak et al. |
| 2011/0124978 A1 | 5/2011 | Williams |
| 2011/0125866 A1 | 5/2011 | Williams |
| 2011/0126143 A1 | 5/2011 | Williams et al. |
| 2011/0130643 A1 | 6/2011 | Derchak et al. |
| 2011/0136627 A1 | 6/2011 | Williams |
| 2011/0137375 A1 | 6/2011 | McBride |
| 2011/0137678 A1 | 6/2011 | Williams |
| 2011/0140890 A1 | 6/2011 | Vock et al. |
| 2011/0140897 A1 | 6/2011 | Purks et al. |
| 2011/0161455 A1 | 6/2011 | Johnson et al. |
| 2011/0191018 A1 | 8/2011 | Werner et al. |
| 2011/0192223 A1 | 8/2011 | Johnson et al. |
| 2011/0196603 A1 | 8/2011 | Graham et al. |
| 2011/0202268 A1 | 8/2011 | Werner et al. |
| 2011/0234556 A1 | 9/2011 | Uehara et al. |
| 2011/0288811 A1* | 11/2011 | Greene ............ 702/141 |
| 2011/0314702 A1 | 12/2011 | Berner, Jr. et al. |
| 2012/0004883 A1 | 1/2012 | Vock et al. |

FOREIGN PATENT DOCUMENTS

| | | |
|---|---|---|
| FR | 2743701 | 7/1997 |
| GB | 1178121 | 1/1970 |
| GB | 2278198 | 11/1994 |
| JP | 11196906 | 7/1999 |

OTHER PUBLICATIONS

Stirling, University of Alberta, Department of Mechanical Engineering, 2004.*

Ardigo et al., "Metabolic and Mechanical Aspects of Foot Landing Type, Forefoot and Rearfoot Strike, in Human Running," Acta Physiol. Scand., 1995, 155, pp. 17-22.

Bobbert et al., "Mechanical Analysis of the Landing Phase in Heel-Toe Running," Journal of Biomechanics, vol. 25, No. 3, pp. 223-234, 1992.

Boyer et al., "'Quantification of the Input Signal for Soft Tissue Vibration During Running," Journal of Biomechanics, 40, (2007), pp. 1877-1880.

Bramble et al., "Endurance Running and the Evolution of Homo," Nature, vol. 432, Nov. 18, 2004, pp. 345-352.

Cavanagh et al., "Ground Reaction Forces in Distance Running," Journal of Biomechanics, vol. 13, pp. 397-406, (1979).

Crowell et al., "Reducing Impact Loading During Running With the Use of . . . ," Journal of Orthopaedic & Sports Physical Therapy, Apr. 2010, vol. 40, No. 4, pp. 206-213.

Cunningham, "What Does . . . ," Proc. 4th World Congr. Ballistocard and Cardiovasc. Dynamics, Amsterdam 1975 Biblthca cardiol. 35: pp. 64-68 (Karger, Basel 1976).

Dallam et al., "Effect of a Global Alteration of Running Technique on Kinematics and Economy," Journal of Sports Sciences, Jul. 2005, 23(7), pp. 757-764.

De Wit et al., "Biomechanical Analysis of the Stance Phase During Barefoot and Shod Running," Journal of Biomechanics, 33 (2000) pp. 269-278.

Divert et al., "Stiffness Adaptions in Shod Running," Journal of Applied Biomechanics, 2005, 21, pp. 311-321.

Divert et al., "Mechanical Comparison of Barefoot and Shod Running," Int. J. of Sports Med., 2005, 26, pp. 593-598.

Divert et al., "Barefoot-Shod Running Differences: Shoe of Mass Effect?," Int. J. of Sports Med., 2008, 29, pp. 512-518.

Eriksson et al., "Immediate Effect of Visual and Auditory Feedback to Control the Running Mechanics . . . ," Journal of Sports Sciences, Feb. 1, 2011, 29(3), pp. 253-262.

Eslami et al., "Forefoot-Rearfoot Coupling Patterns and Tibial Internal Rotation During Stance Phase of Barefoot Versus . . . ," Clinical Biomechanics, 22, (2007), pp. 74-80.

Fong et al., "Cushioning and Lateral Stability Functions of Cloth Sport Shoes," Sports Biomechanics, Sep. 2007, 6(3), pp. 407-417.

Gerritsen et al., "Direct Dynamics Simulation of the Impact Phase in Heel-Toe Running," Journal of Biomechanics, vol. 28, No. 6, pp. 661-668, 1995.

Hamill et al., "Effects of Shoe Type on Cardiorespiratory Responses . . . ," Medicine and Science in Sport and Exercise, vol. 20, No. 5, 1988, pp. 515-521.

Hamill et al., "Impact Characteristics in Shod and Barefoot Running," Footwear Science, vol. 3, No. 1, Mar. 2011, pp. 33-40.

Hasegawa et al., "Foot Strike Patterns of Runners at the 15-KM Point During . . . ," Journal of Strength and Conditioning Research, 2007, 21(3), pp. 888-893.

Hreljac, "Impact and . . . ," Official Journal of the American College of Sports Science, Medicine & Science in Sport & Exercise, 0195-9131/04/3605-0845, 2004, pp. 845-849.

(56) References Cited

OTHER PUBLICATIONS

Kerr et al., "Footstrike Patterns . . . ," Proceedings of the International Symposium on Biomechanical Aspects of Sport Shoes & Playing Surfaces, U. of Calgary, Aug. 1983.
Kersting, "Regulation of Impact Forces During Treadmill Running," Footwear Science, vol. 3, No. 1, Mar. 2011; pp. 59-68.
Laughton et al., "Effect of Strike Pattern and Orthotic Intervention on Tibial Shock During Running," Journal of Applied Biomechanics, 2003, 19, pp. 153-168.
Lieberman et al., "Foot Strike Patterns and Collision Forces in Habitually Barefoot Versus Shod Runners," Nature, vol. 463, Jan. 28, 2010, pp. 531-536.
Magill, "The Influence of Augmented Feedback on Skill Learning Depends on Characteristics of the Skill and the Learner," QUEST, 1994, 46, pp. 314-327.
Mercer et al., "Relationship Between Shock Attenuation and Stride Length During Running at Different Velocities," Eur. J. Appl. Physiol., (2002), 87, pp. 403-408.
Messier et al., "Effects of a Verbal and Visual Feedback System on Running Technique, Perceived . . . ," Journal of Sports Sciences, 1989, 7, pp. 113-126.
Newham et al., "Pain and Fatigue after Concentric and Eccentric Muscle Contractions," Clinical Science, (1983), 64, pp. 55-62.
Nokes et al., "Vibration Analysis of Human Tibia: The Effect of Soft Tissue on the Output from Skin-Mounted . . . ," J.Biomed. Eng. 1984, vol. 6, July, pp. 223-226.
Proske et al., "Muscle Damage From Eccentric Exercise: Mechanism, Mechanical Signs, Adaptation and Clinical . . . ," Journal of Physiology, (2011), 537.2, pp. 333-345.
Salmoni et al., "Knowledge of Results and Motor Learning: A Review and Critical Reappraisal," Psychological Bulletin, 1984, vol. 95, No. 3, pp. 355-386.
Shorten et al., "Spectral Analysis of Impact Shock During Running," International Journal of Sport Biomechanics, vol. 8, 1992, pp. 288-304.
Shorten et al., "The 'Heel Impact' Force Peak During Running is Neither 'Heel' nor 'Impact' and Does Not . . . ," Footwear Science, vol. 3, No. 1, Mar. 2011, pp. 41-58.
Squadrone et al., "Biomechanical and Physiological Comparison of Barefoot . . . ," Journal of Sports Medicine and Physical Fitness, Mar. 2009, vol. 49, No. 1. pp. 6-13.
Stackhouse et al., "Orthotic Intervention in Forefoot and Rearfoot Strike Running Patterns," Clinical Biomechanics 19, (2004), pp. 64-70.
Williams et al., "Relationship Between Distance Running Mechanics, Running Economy, and . . . ," Journal of Applied Physiology, vol. 63, Issue 3, (1987), pp. 1236-1245.
Williams et al., "Lower Extremity Mechanics in Runners with a Converted Forefoot Strike Pattern," Journal of Applied Biomechanics, 2000, 16, pp. 210-218.
Wright et al., "Passive Regulation of Impact Forces in Heel-Toe Running," Clinical Biomechanics, 13, (1998), pp. 521-531.
International Search Report and Written Opinion for PCT/US2012/024147, mailed on May 10, 2012.

\* cited by examiner

SYSTEMS AND METHODS FOR MONITORING ATHLETIC PERFORMANCE

CROSS-REFERENCE TO RELATED APPLICATIONS

This application claims priority to and the benefit of U.S. Provisional Patent Application Ser. No. 61/440,243, filed Feb. 7, 2011, the disclosure of which is incorporated herein by reference in its entirety.

FIELD OF THE INVENTION

The present invention relates generally to the field of athletic equipment, and more particularly to systems and methods for providing training information to a runner.

BACKGROUND OF THE INVENTION

A number of devices exist for providing a runner with basic training information. For example, systems for measuring and recording the heart rate, speed, distance, and/or stride rate of a runner using a sensor that may be clipped, for example, to workout apparel has been manufactured by adidas AG of Herzogenaurach, Germany. Similarly, Nike Inc., of Beaverton, Oreg., has produced devices that measure and record the distance and pace of a walk or run. Such devices often consist of small accelerometers attached to or embedded in a shoe, which communicate with a receiving device (e.g., a sportband or a receiver plugged into of embedded within a mobile phone). The device and receiver allow a user to track the distance, time, and pace of a training run, with the information provided to a user through audio feedback during the training run and/or recorded for later analysis. Systems also exist for measuring and recording training information such as distance, time, and pace of a training run through utilization of a mobile phone of GPS ("Global Positioning System") device without the need for a sensor in a shoe.

However, these systems only provide basic training information related, for example, to the speed and distance travelled by a runner, and cannot provide any detailed biofeedback information that may be used to improve the actual running form and technique of the runner. As a result, there still exists a need for a system and method capable of providing detailed training information to an athlete during and after a training session to assist in improving their running form.

SUMMARY OF THE INVENTION

The present invention is directed towards novel systems, methods and devices for monitoring one or more athletic performance characteristic of a user and/or providing biofeedback information to the user to assist in training the user to run with better form and, for example, with an improved foot strike.

One aspect of the invention includes an apparatus for monitoring one or more athletic performance characteristic of a user, the apparatus including a sensing unit adapted to be attachable to a shoe of a user. The sensing unit includes a first sensor, such as a gyroscopic sensor, that is adapted to monitor a movement of a foot of the user while the user is in motion, processing means for determining a first performance characteristic of the user, such as a foot strike location of a foot of the user upon striking a ground surface, and transmitting means for transmitting a data package representative of the performance characteristic to a remote receiver. The gyroscopic sensor may be adapted to measure an angular velocity of the foot of the user. The means for determining a performance characteristic of the user may include a microprocessor.

In one embodiment the apparatus also includes receiving means for receiving the data package transmitted from the sensing unit and communicating information representative of the performance characteristic to the user. The means for communicating information to the user may include, or consist essentially of, at least one of a visual signal, an auditory signal, and/or a tactile signal (e.g., a vibration). The information may be communicated to the user in substantially real-time and/or be stored, for example within the sensing unit and/or the receiving means, for communicating to the user at a later time and/or for further analysis.

The receiving means may include one or more remote user feedback devices, such as, but not limited to, a watch, a detachable strap, a mobile phone, an earpiece, a hand-held feedback device, a laptop computer, head-mounted feedback device (e.g., a visor or hat), and/or a desktop personal computer. Alternatively, or in addition, the receiving means may include a software application and/or hardware (e.g., a dongle) for controlling at least one function of a remote user feedback device, such as a mobile phone.

In one embodiment, the sensing unit includes a housing unit adapted to house the first sensor, the processing means, and the transmitting means. The housing unit may be adapted to be releasably attachable to a sole and/or upper of the shoe of the user, or be fixedly attached to, or embedded within, an upper and/or sole of the shoe. In one embodiment the housing unit is releasably attachable to at least one of a fastening portion (e.g., the lacing portion) of a shoe or a heel portion of the shoe.

The apparatus may include means for determining at least one second performance characteristic of the user, which can be based upon an output from the first sensor and/or be based upon an output from one or more second sensor(s). The second sensor(s) may include, or consist essentially of, one or more accelerometers, pressure sensors, force sensors, temperature sensors, chemical sensors, global positioning systems, piezoelectric sensors, rotary position sensors, gyroscopic sensors, heart-rate sensors, and/or goniometers. Other sensors, such as, but not limited to, electrocardiograph sensors, electrodermograph sensors, electroencephalograph sensors, electromyography sensors, feedback thermometer sensors, photoplethysmograph sensors, and/or pneumograph sensors may also be utilized in various embodiments of the invention. The at least one second performance characteristic may include, or consist essentially of, at least one of a cadence, a posture, a lean, a speed, a distance travelled, and/or a heart rate of the user.

In one embodiment, the processing means includes a comparison of a localized maximum angular velocity measurement and a localized minimum angular velocity measurement during a foot strike event (e.g., during a brief period immediately before, at, and/or after initial contact between a foot and the ground). For example, processing the measured data may include, or consist essentially of, dividing the localized minimum angular velocity measurement during a foot strike event by the localized maximum angular velocity measurement during a foot strike event, and comparing the resulting calculated value with at least one predetermined comparison value to determine whether a heel strike, a midfoot strike, or a forefoot strike has occurred. Alternatively, or in addition, the processing means may include integration of measured angular velocity data during a foot strike event and comparison of the integrated positive angular velocity results and the integrated negative angular velocity results during a foot strike event.

Another aspect of the invention includes a method for monitoring one or more athletic performance characteristic of a user, the method including providing a sensing unit adapted to be attachable to a shoe of a user. The sensing unit may include a first sensor, such as a gyroscopic sensor, that is adapted to monitor a movement of a foot of the user while the user is in motion, processing means for determining a first performance characteristic of the user, such as a foot strike location of a foot of the user upon striking a ground surface, and transmitting means for transmitting a data package representative of the performance characteristic to a remote receiver. The method further includes providing receiving means for receiving a data package transmitted from the sensing unit and communicating information representative of the performance characteristic to the user. In one embodiment, the method allows for the communication of the information to the user in substantially real-time.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1:
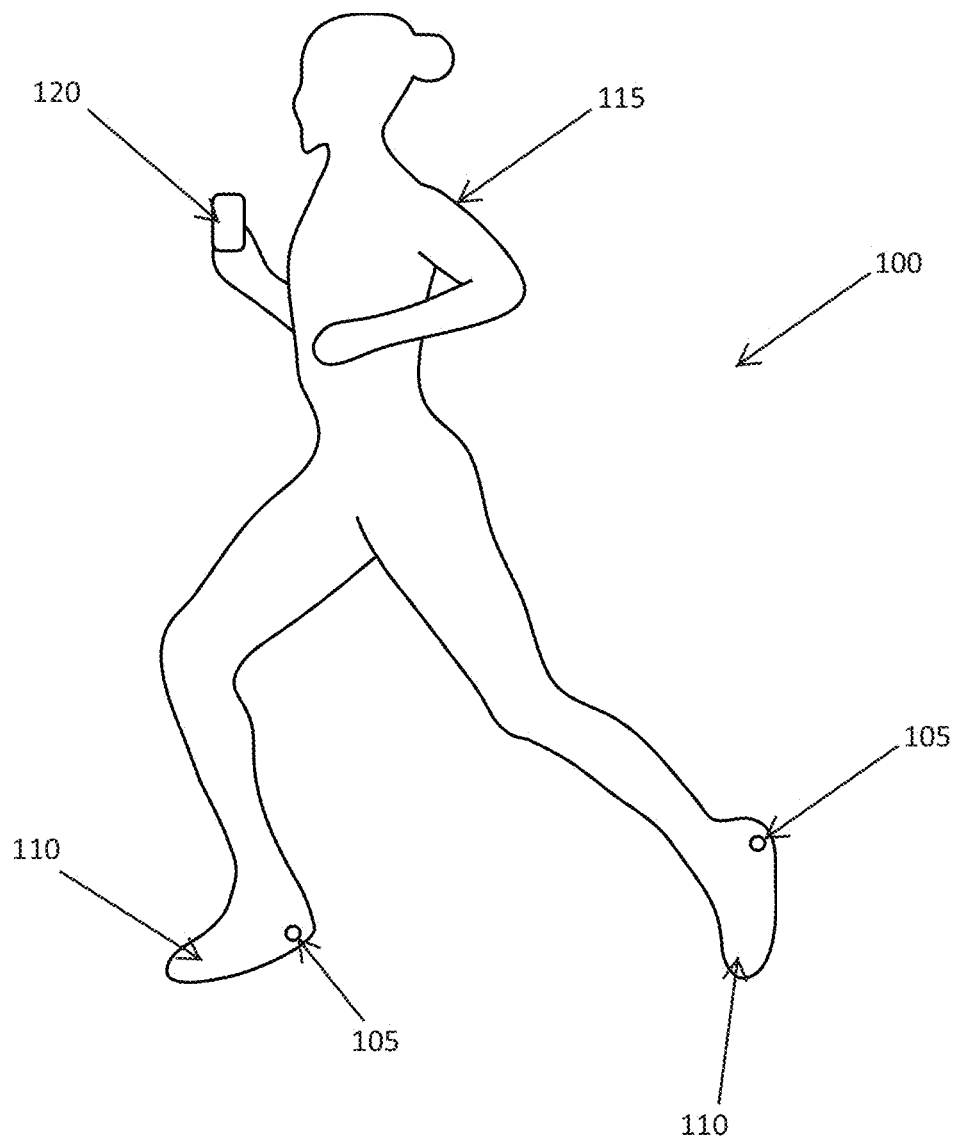
FIG. 1 is a schematic perspective view of a biofeedback system as worn by a runner, in accordance with one embodiment of the invention.

The invention described herein relates generally to improved biofeedback systems, and related methods, for use in training users (e.g., runners or other athletes) to run with an improved running form or technique. The invention may be utilized by runners or other athletes of all levels of skill from professional athletes through to beginners and occasional joggers. By placing one or more sensors on the body of a runner (e.g., on or in one or more shoe and/or piece of apparel), the systems and methods described herein may be used as a coaching tool to provide substantially instantaneous feedback and coaching during athletic activity, and also store information for evaluation and further processing after the run.

Promoting better running form may be beneficial to a runner for a number of reasons such as, but not limited to, improving running efficiency (thereby increasing performance) and reducing the risk of injury. In general, coaching can be an important way to promote proper running form and keep runners injury free. However the majority of runners (including many collegiate and even some elite runners) have never been given any or significant training on how to run with proper form. As a result, many runners are unaware of problems with their running form (e.g., an improper foot strike position or a running style wherein a runner's right foot contacts the ground differently than their left foot) that may significantly affect their running efficiency and leave them more prone to injury.

The utilization of high-speed cameras during coaching may provide a runner with some feedback to assist in improving running form. However, not only do the majority of athletes not have sufficient access to professional coaching utilizing such technology to provide any substantive guidance to train them to run with an improved running form, but such coaching, even if available, can be expensive and time consuming. In addition, watching video of an athlete running does not provide instantaneous feedback that can be used by the athlete during a run. While technology has been utilized to provide some instantaneous feedback to a runner, such as the speed, distance travelled, heart rate, and calories burned during a run, the information provided by these systems does not produce biofeedback information that may be used to give a runner substantive training on proper running form. The inventions described herein address this issue by providing improved systems, and related methods, for measuring, transmitting, storing, analyzing, and/or communicating substantive biofeedback data that may be utilized instantaneously, or substantially instantaneously, to promote good running form in an athlete during and/or after a run.

Biofeedback information of use in training an athlete to run with proper running form includes, but is not limited to, foot strike position, cadence, posture, and lean information. Such information may be used to analyze a runner's technique and running traits, and identify parameters that can be adjusted by a runner during training to improve one or more performance characteristic. Good running form for an athlete may include elements such as, but not limited to, quick strides, a midfoot foot strike location, and good posture. These elements may increase the efficiency and ease of running while reducing stresses on the runner that could result in strains and other injuries. In contrast, poor running form, which is common in untrained athletes, may include elements such as overstriding, aggressive heel-striking, and bad posture. These poor running elements may, for example, produce excessive stresses to the knee, potentially resulting in Runner's Knee/Petellofemoral Pain Syndrome or other injuries.

The posture of a runner relates to the carriage of the body of the runner during running. Good posture (generally an up-right posture) may be achieved, for example, by standing tall and running with your head up and with your gaze directed straight ahead.

The cadence of a runner (i.e., the number of foot strikes per minute) may be important in ensuring good running form. In one embodiment, a cadence of about 180 foot strikes per minute may be optimal to prevent over-striding and to ensure proper running form regardless of the pace of the runner. In alternative embodiments higher or lower cadences may be used depending, for example, on the specific physiology, age, and/or goals of the user.

The lean of a runner may be utilized to reduce the need for excessive muscle force by advantageously utilizing gravity to assist in forward motion. In one embodiment, improved lean may be achieved by utilizing a running style including a forward lean over the whole length of the body without bending at the waist and by flexing at the ankle to reduce unnecessary muscle strain caused by toeing-off.

The foot strike location (i.e., the location, on the sole of the foot, of initial impact with a ground surface during each step) can be extremely important in promoting a good running form. Runners with a midfoot striking gait distribute pressure across the foot during a running gait cycle differently than runners employing a heel striking gait. In addition, the mechanical work performed by the lower extremity of a runner using a midfoot striking gait is distributed across the joints differently than a runner employing a heel striking gait. Runners with a midfoot striking gait primarily have pressure distributed in the lateral midfoot and forefoot region of the foot at initial impact and exhibit more ankle flexion (dorsiflexion) subsequent to the initial impact. Runners with a heel striking gait primarily have pressure distributed in the lateral heel at initial impact and generally do not exhibit as much ankle flexion after impact. As a result, heel strikers tend to have larger stresses placed on their knee which can lead to injuries such as Runner's Knee/Patellofemoral Pain Syndrome. Consequently, rearfoot/heel strikers potentially have a less efficient running gait than midfoot strikers, with heel striking and overstriding often causing braking. An example shoe conducive to a midfoot striking gait is described in U.S. Patent Publication No. 2009-0145005, the disclosure of which is incorporated herein by reference in its entirety. In addition, a midfoot striking gait may provide a superior running form than a pronounced forefoot running gait (which may, for example, cause calf-strain and Achilles strain). One embodiment of the invention may include the use of one or more sensors to determine the location, on the sole of the foot, of initial impact with a ground surface during each step, and/or determine that angle of the foot with respect to the ground surface at initial impact (which may be used to determine foot strike location).

One embodiment of the invention includes a system 100 for providing biofeedback information to a runner 115 for use in improving running form. The system 100, as shown in FIG. 1, includes one or more sensors 105 attached to (e.g., embedded within, fixedly coupled to, or releasably coupled to) a portion of a shoe 110 of a runner 115 to measure one or more data conditions/performance characteristics during athletic activity (e.g., a run). The system 100 also includes one or more remote receiving systems 120 for receiving data from the sensor(s) 105 and communicating information to the runner based on an analysis of the gathered data. The analysis of the gathered data may be carried out in a processor located in the shoe 110, the remote receiving system 120, and/or a separate analyzing unit (e.g., a personal computer). One or more sensors 105 can be placed in each shoe 110 of the runner 115, or in only a single shoe 110 of the runner 115.

The sensor(s) may be integrally embedded within the shoe and, for example, within one or more portions of a sole (e.g., an outsole, midsole, or insole) of a shoe. One or more sensors may also be integrally embedded within one or more portions of an upper of a shoe. In another embodiment, one or more sensors may be releasably attachable to a portion of the sole and/or upper of a shoe. For example, a sensor unit may be adapted to clip to a portion of an upper of a shoe (e.g., an outer mesh layer of the shoe or a lacing section of the shoe), and/or be releasably attached to a portion of a sole of the shoe. The sensor(s) may be releasably attached through any appropriate attaching elements including, but not limited to, a hook and loop fastening (e.g., Velcro®), a clip, a pin, lacing, magnetic elements, and/or an adhesive.

Various sensors may be utilized to measure one or more data conditions during athletic activity. Example sensors include, but are not limited to, mechanical feedback devices (e.g., retractable pins that retract upon contact with the ground to measure and indicate a ground contact and/or a force associated therewith, or pins or other structures that provide a tactile sensation to a user during foot strike), accelerometers, piezoelectric sensors, rotary position sensors, gyroscopic sensors, temperature sensors, chemical sensors (e.g., sensors for measuring oxygen levels), GPS devices, pressure sensors (e.g., pressure transducers), force sensors (e.g., load cells, force transducers, or stress/strain sensors), and/or goniometers. Example pressure/force sensors include, but are not limited to, resistive, capacitive, impedance based, and/or piezoelectric sensors. The sensors may measure data conditions at a localized position or be strips or pads adapted to measure data conditions (e.g., pressure and/or force) over an extended area. In various embodiments other electromagnetic, mechanical, and/or optical sensors may be used in addition to, or in place of, the sensors listed above.

Figure 2:
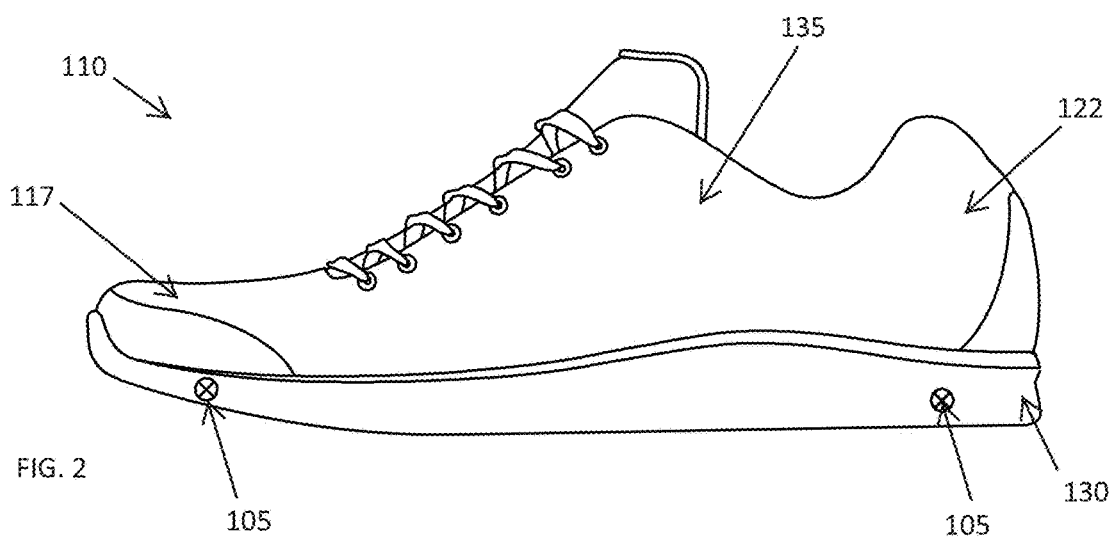
FIG. 2 is a schematic side view of a shoe with forefoot and heel sensors embedded therein, in accordance with one embodiment of the invention.
Figure 3:
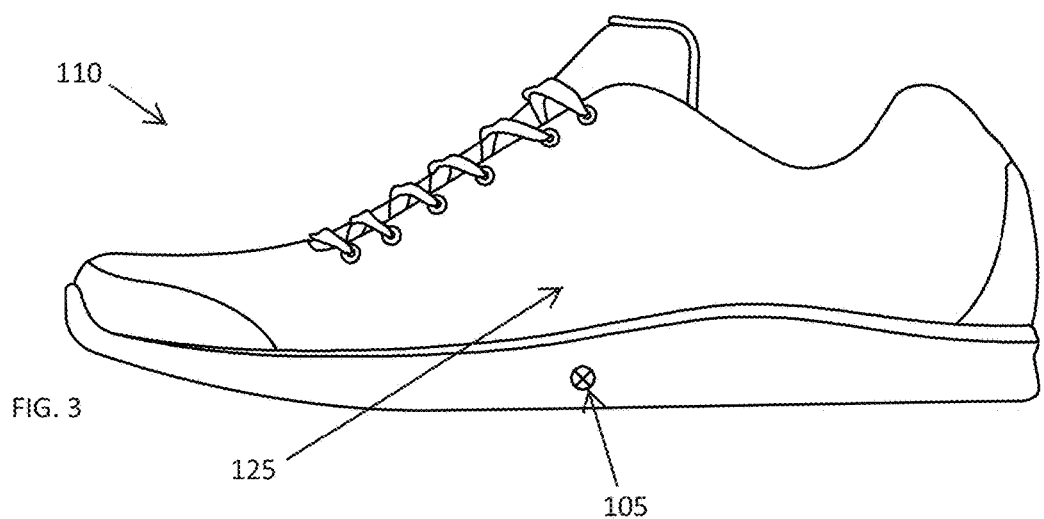
FIG. 3 is a schematic side view of a shoe with a midfoot sensor embedded therein, in accordance with one embodiment of the invention.

One or more sensors may be placed at any appropriate location on the shoe and, for example, within a forefoot portion, a midfoot portion, and/or a heel portion of a shoe sole and/or upper. In one embodiment, as shown in FIG. 2, a shoe 110 includes a forefoot sensor 105 located in a forefoot portion 117 of the shoe 110, and a heel sensor 105 located within a heel portion 122 of the shoe 110. Sensors may be placed at other locations on the shoe 110 in addition to, or in place of, the forefoot portion 117 and heel portion 122. For example, one or more midfoot sensors 105 may be located at a midfoot portion 125 of a shoe 110, as shown in FIG. 3. The various sensors 105 may be positioned within or above a sole 130 of the shoe 110 (e.g., within a cavity in the midsole of the shoe or in an insole place within the shoe) and/or be positioned within or on an upper 135 of a shoe 110.

Figure 4:
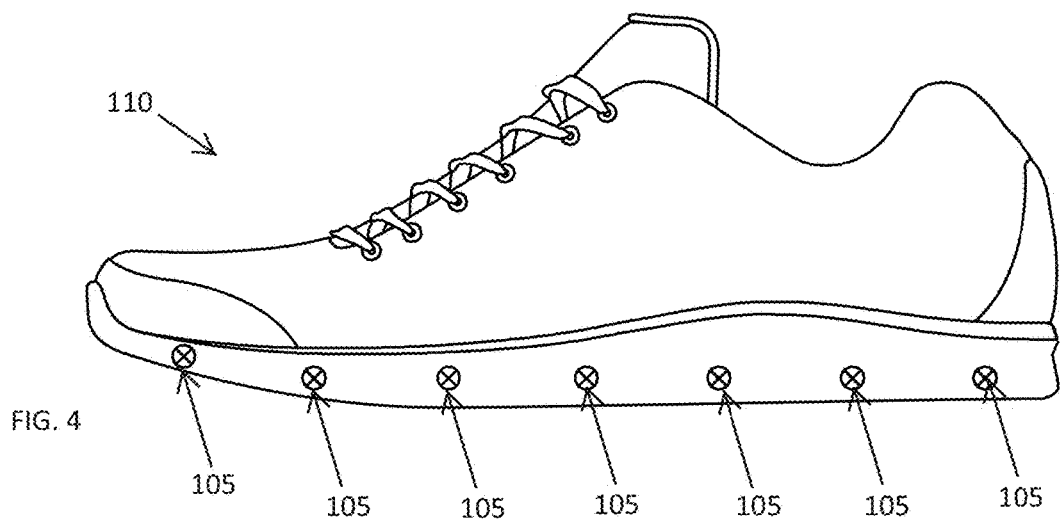
FIG. 4 is a schematic side view of a shoe with a plurality of sensors embedded therein, in accordance with one embodiment of the invention.
Figure 5:
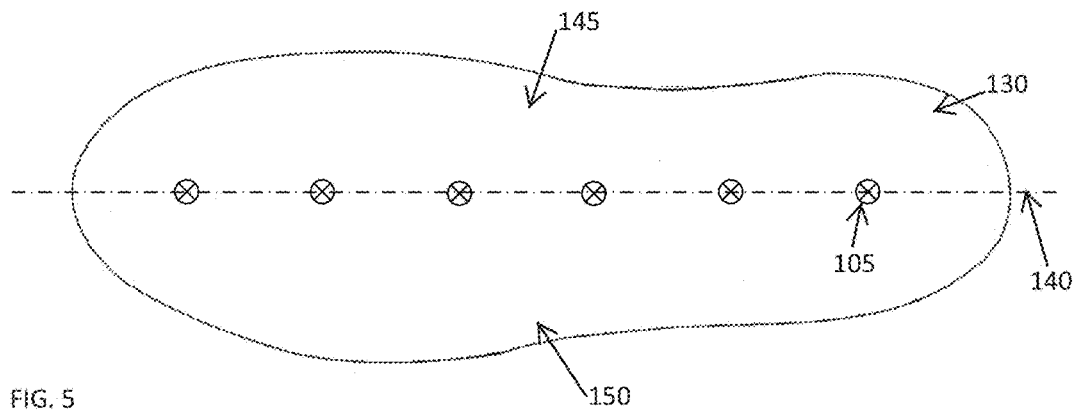
FIG. 5 is a schematic plan view of a shoe with an array of sensors embedded therein, in accordance with one embodiment of the invention.
Figure 6:
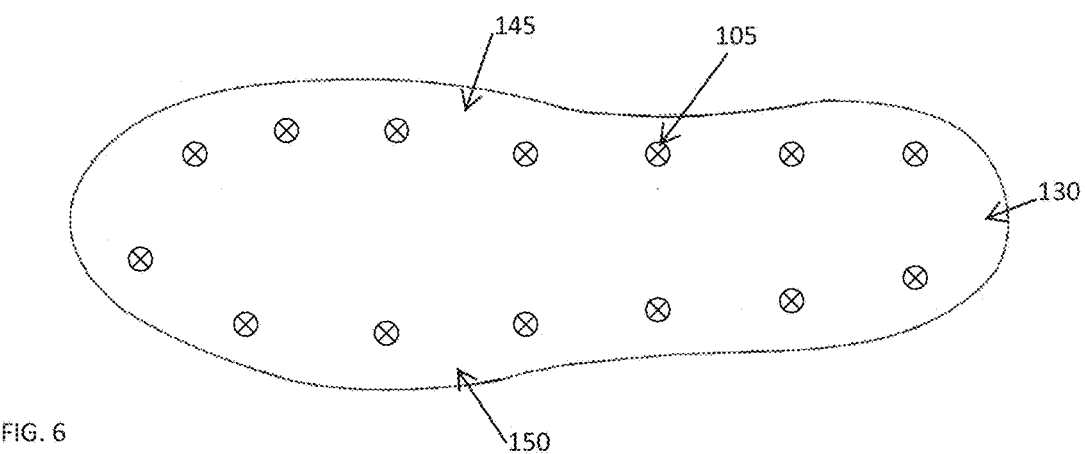
FIG. 6 is a schematic plan view of another shoe with an array of sensors embedded therein, in accordance with one embodiment of the invention.

In one embodiment, a plurality of sensors 105 (i.e., a sensor array) are positioned at various locations along a length of the shoe 110, or a portion thereof, as shown in FIG. 4. These sensors 105 may be positioned at a number of locations substantially along a central axis 140 of the sole 130, as shown in FIG. 5, or at a number of locations along a medial side 145 and/or a lateral side 150 of the sole 130, as shown in FIG. 6. Any appropriate number of sensors 105 may be positioned at any appropriate locations over the length and width of the sole 130 of the shoe 110, with the sensors 105 embedded within, or releasably attached to, an outsole, midsole, and/or insole of the sole 130, depending upon the specific data and running traits being measured. In one embodiment, one or more of the sensors 105 may be exposed on an outer surface of the sole 130. Alternatively, or in addition, one or more of the sensors 105 may be embedded within the sole 130.

Figure 7:
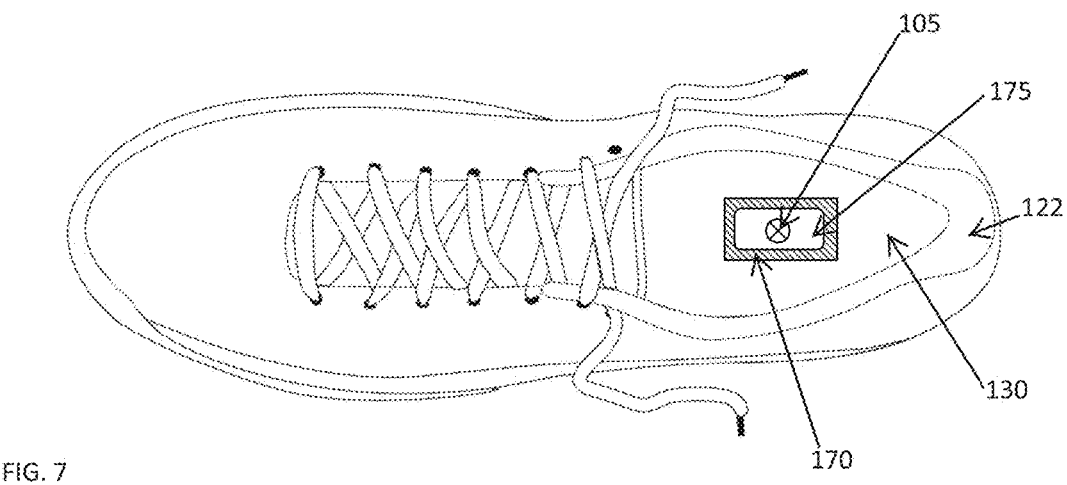
FIG. 7 is a schematic plan view of a shoe with an sensor holding insert inserted within the sole, in accordance with one embodiment of the invention.

In one embodiment, one or more sensors 105 may be placed in a removable insert that may be positioned inside a shoe, for example as a removable insole or as an insert adapted to fit within a cavity or pocket formed within a portion of the shoe sole or upper (e.g., in a heel pocket of tongue pocket). For example, a shoe 110 may be formed with a sole portion 130 having a cavity 170 adapted to releasably receive an insert 175 holding one or more sensors 105 therein, as shown in FIG. 7. The cavity may include a covering portion adapted to cover and protect the insert during operation. The cavity 170, or cavities, may be placed at any location within the forefoot portion 117, midfoot portion 125, and/or heel portion 122 of the shoe 110. In various embodiments the cavity 170 may be accessed from the interior of the shoe, as shown in FIG. 7, or through an opening in an outer surface of the outsole 130 of the shoe 110.

Figure 8:
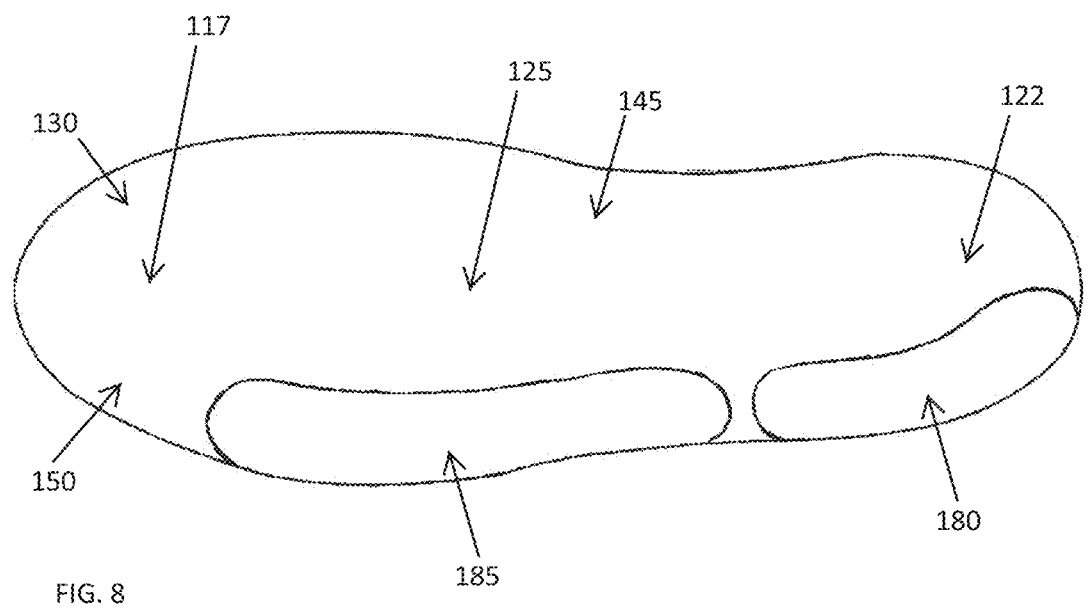
FIG. 8 is a schematic plan view of a shoe sole having midfoot and heel sensor pads, in accordance with one embodiment of the invention.
Figure 9:
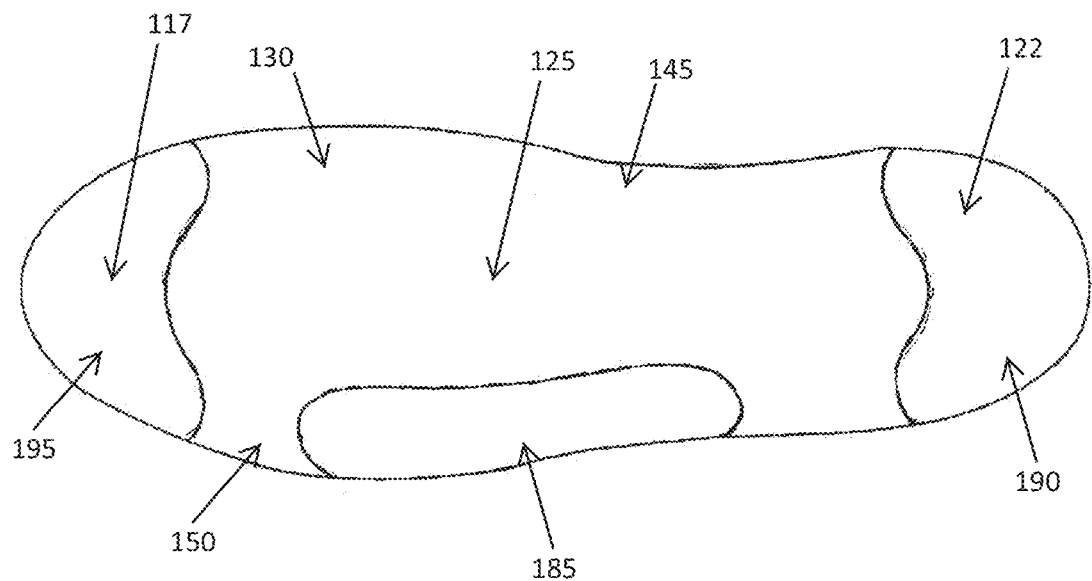
FIG. 9 is a schematic plan view of a shoe sole having forefoot, midfoot, and heel sensor pads, in accordance with one embodiment of the invention.

In one embodiment, one or more sensor pads or strips may be affixed to, or embedded in, a sole 130 of a shoe 110. For example, FIG. 8 shows a sole 130 having a heel sensor pad 180 located at a heel portion 122 along a lateral side 150 of the sole 130, with a midfoot sensor pad 185 located at a midfoot portion 125 along the lateral side 150 of the sole 130. Sensor pads or strips can be positioned along a medial side, lateral side, and/or central portion of the sole, or span across a width of the shoe, or a portion thereof. For example, FIG. 9 shows a sole 130 having a midfoot sensor pad 185 located at a midfoot portion 125 along the lateral side 150 of the sole 130, but also having a heel sensor pad 190 spanning across the width of the heel portion 122 and a forefoot sensor pad 195 spanning across the width of forefoot portion 117.

In various embodiments sensor pads and/or strips may be positioned on any portion of the shoe sole. The sensor pads or strips can be embedded within an outsole, midsole, and/or insole, or be positioned between adjoining layers of the sole. Alternatively, the sensor pads or strips can be located in a removable insert (e.g., a removable insole) that can be placed into the shoe, or attached to an exterior, ground contacting, surface of the sole.

Figure 10:
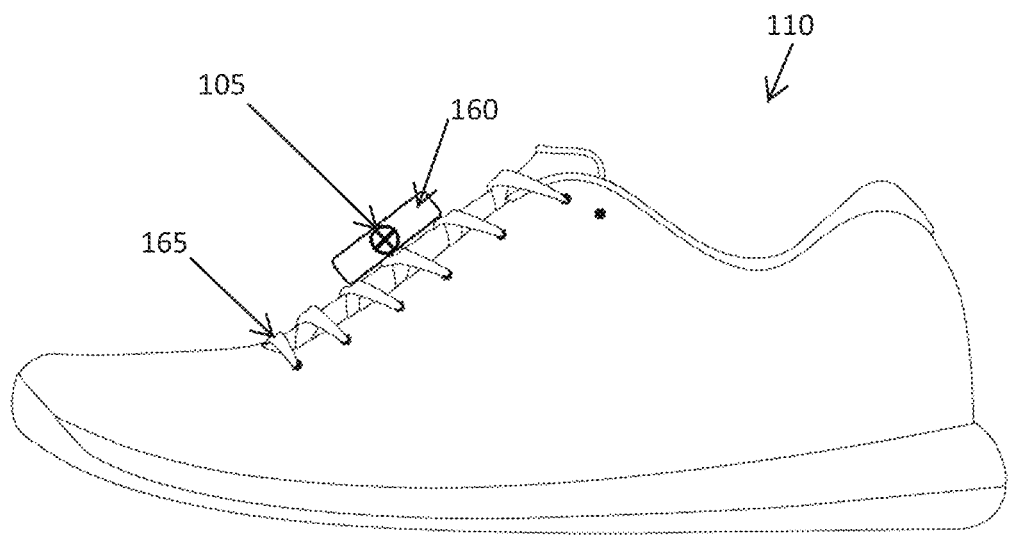
FIG. 10 is a schematic side view of a shoe with a sensor holding insert coupled to the shoe at a lacing portion, in accordance with one embodiment of the invention.
Figure 11:
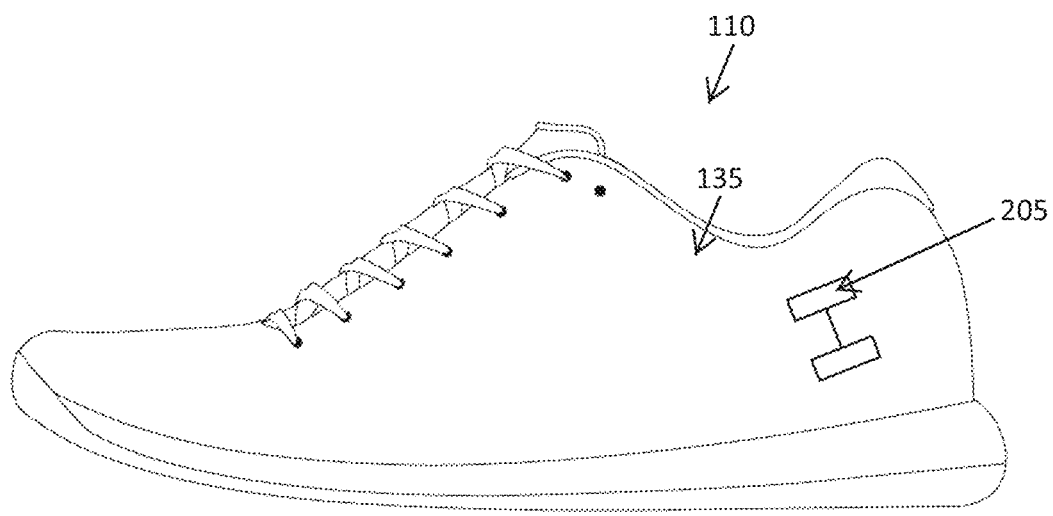
FIG. 11 is a schematic side view of a shoe with a sensor coupled to the upper, in accordance with one embodiment of the invention.

Alternatively, one or more sensors 105 may be placed within an insert 160 that may be releasably attached to the shoe 110 at a lacing portion 165, as shown in FIG. 10, or on one or more portions of an upper 135 of the shoe 110, as shown in FIG. 11.

The sensors 105 may be used to measure the location and distribution of each foot strike of each foot on the ground during running and/or the force and/or pressure applied to various portions of the foot during running. The measured data may be processed to produce biofeedback information that may be used to train a runner to run with a more efficient and safer foot strike location, such as with a midfoot strike. The data may be processed and communicated to a runner instantaneously, or substantially instantaneously, to give the runner immediate feedback during a run. The data may also be stored and used to generate both mean and time dependent results after the run is completed, thereby providing a runner and/or a coach with a full analysis of the runner's performance over the course of the run.

The sensors 105 may also be used to measure the cadence of the runner during a run, in addition to, or instead of, the foot strike information, by recording the time between each foot strike. Again, the measured data may be processed and communicated to a runner instantaneously, or substantially instantaneously, to give the runner immediate feedback during a run and/or be stored and used to generate both mean and time dependent results after the run is completed.

In one example embodiment, a shoe 110 may include a sensor 105 comprising a mechanical feedback device (e.g., a pin) located in a sole of a shoe 110 and, for example at the heel portion. Data measured and transmitted from the sensor 105 can be used to determine when a runners heel is in contact with the ground, thereby producing information that can be used to provide the runner with a better awareness of their gait.

One embodiment of the invention includes one or more sensors 205 positioned either in or on the upper 135 or sole 130 of a shoe 110 (as described hereinabove for the sensors 105) to measure data that can be utilized to determine a runner's posture and/or lean during a run. For example, one or more sensors 205 (e.g., goniometers) can be fixedly embedded or releasably attached to an upper 135 of a shoe 110 to measure data that can be processed to provide biofeedback information related to a runners posture and/or lean, as shown in FIG. 11. The sensors 205 may operate independently from, or in concert with, sensors 105 for measuring foot strike and/or cadence. In one embodiment, the sensors 205 can communicate data to a remote receiver using the same transmitter as utilized by the sensors 105. Alternatively, the sensors 205 may utilize a separate transmitter. In an alternative embodiment, sensors for measuring the posture and/or lean of the user may be positioned at other locations on a body of a user (e.g., on an ankle, leg, waist, arm, or chest of the user).

In one embodiment, one or more sensors can be embedded within, or releasably attachable to, an item of apparel wearable by a runner. Alternatively, or in addition, one or more sensors can be mounted on a strap that may be worn by a runner, or removably affixed to a portion of a runner by a skin sensitive adhesive or tape. These sensors can be used in addition to, or in place of, sensors on a shoe to provide biofeedback information related to a performance characteristic of a runner.

In addition to providing biofeedback information related to a runners proper running form (e.g., foot strike, cadence, posture, and/or lean information), the systems described herein may include sensors for measuring other parameters related to a runners performance including, but not limited to, distance, pace, time, calories burned, heart rate, breaths per minute, blood lactate and/or muscle activity (EMG). For example, measuring blood lactate levels may be of use in determining lactate threshold data in long-distance runners and other athletes.

In various embodiments, the sensors 105, 205 may be powered by one or more battery elements coupled to the sensors 105, 205. The batteries may be single use, replaceable batteries or be rechargeable batteries. The rechargeable batteries may be recharged by any appropriate means. Alternatively, the sensors 105, 205 may utilize the biomechanical action of a runner for power.

The sensors 105, 205 may be coupled to one or more transmitters for transmitting measured data to a remote receiver. The transmitter may include, or consist essentially of, a wireless transmitter and, more particularly, a radio frequency transmitter and/or an infrared transmitter. For example, the transmitter may be a radio transmitter adapted to transmit short wavelength radio transmissions via Bluetooth®, Bluetooth® Low Energy, and/or ANT or ANT+ protocols. In one embodiment the system may include a transmitting system capable of transmitting over a plurality of transmission protocols, thereby allowing the device to communicate with multiple different receiving systems. The transmitter may also, in one embodiment, be capable of receiving information transmitted from a remote source. This information may be utilized, for example, to turn on/off the sensors, calibrate the sensors, and/or control one or more function of the sensing system.

Figure 12:
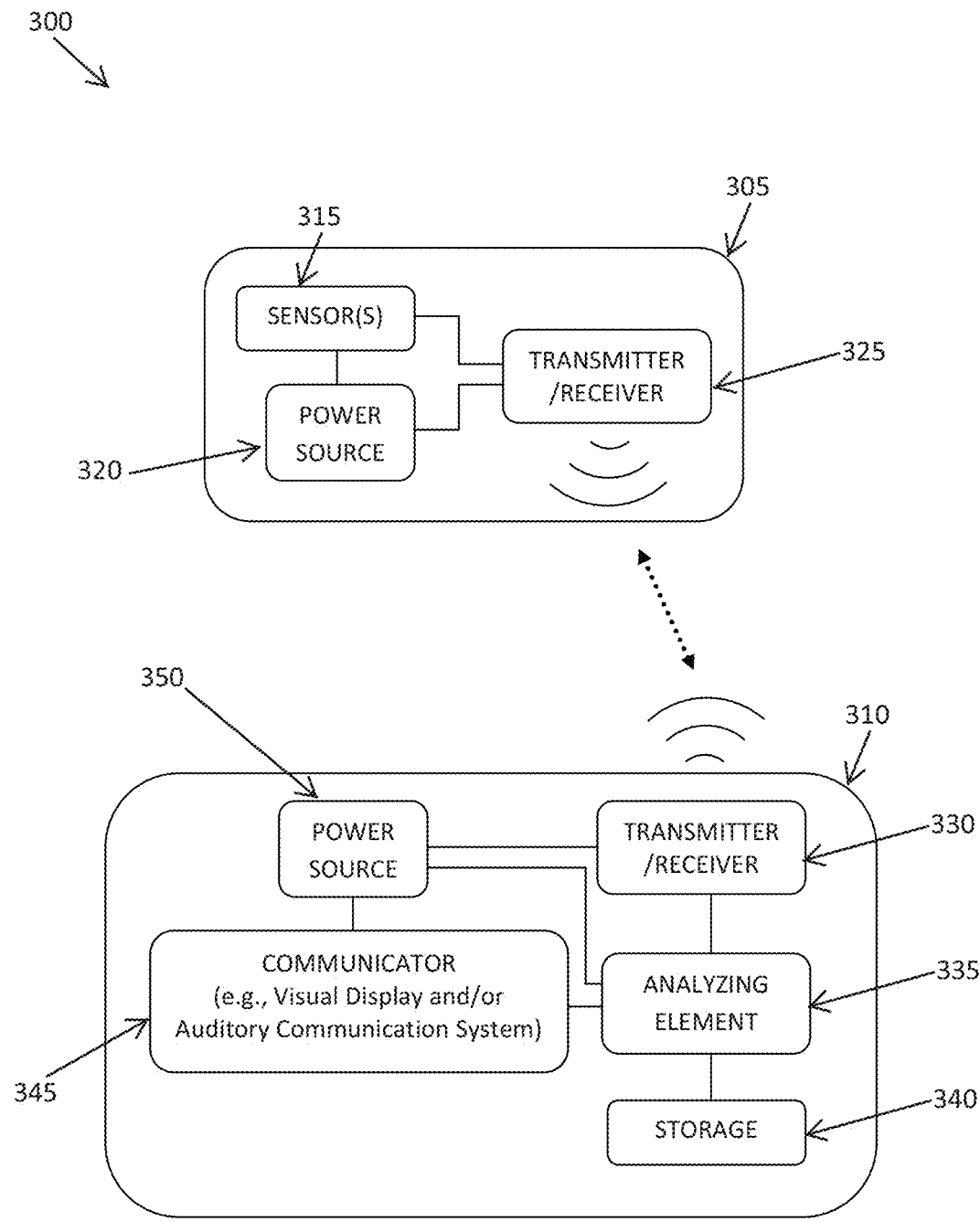
FIG. 12 is a schematic view of a system for providing biofeedback information for an athlete, in accordance with one embodiment of the invention.

The data measured by the sensors in or on the shoe/s) can be transmitted to a remote receiving system for recording and/or analysis. An example system 300 for providing biofeedback information including both a sensing unit 305 and a receiving/analyzing unit 310 is shown in FIG. 12. The sensing unit 305 can include elements such as, but not limited to, one or more sensors 315, a power source 320, and a transmitting/receiving element 325. The sensing unit 305 can be positioned in or on a shoe and/or piece of apparel (as described herein). The remote receiving unit 310 can include elements such as, but not limited to, a transmitting/receiving element 330 for receiving the transmitted data from the sensing unit 305, a remote user feedback element 335 for receiving the data, a storage unit 340 for storing raw and/or analyzed data, a communication element 345 (e.g., a visual display such as a graphical user interface (GUI), an auditory communication element, and/or a tactile user interface) for communicating biofeedback information determined from the analyzed data to an athlete, and a power source 350. The transmitting/receiving element 330 can also be used to communicate with a remote database, such as an online database for an online running/coaching community, thereby allowing biofeedback information to be transmitted to the remote database and allowing biofeedback information, training instructions, software updates, or other digital information to be transmitted from the remote database to the receiving/analyzing unit 310.

Figure 13:
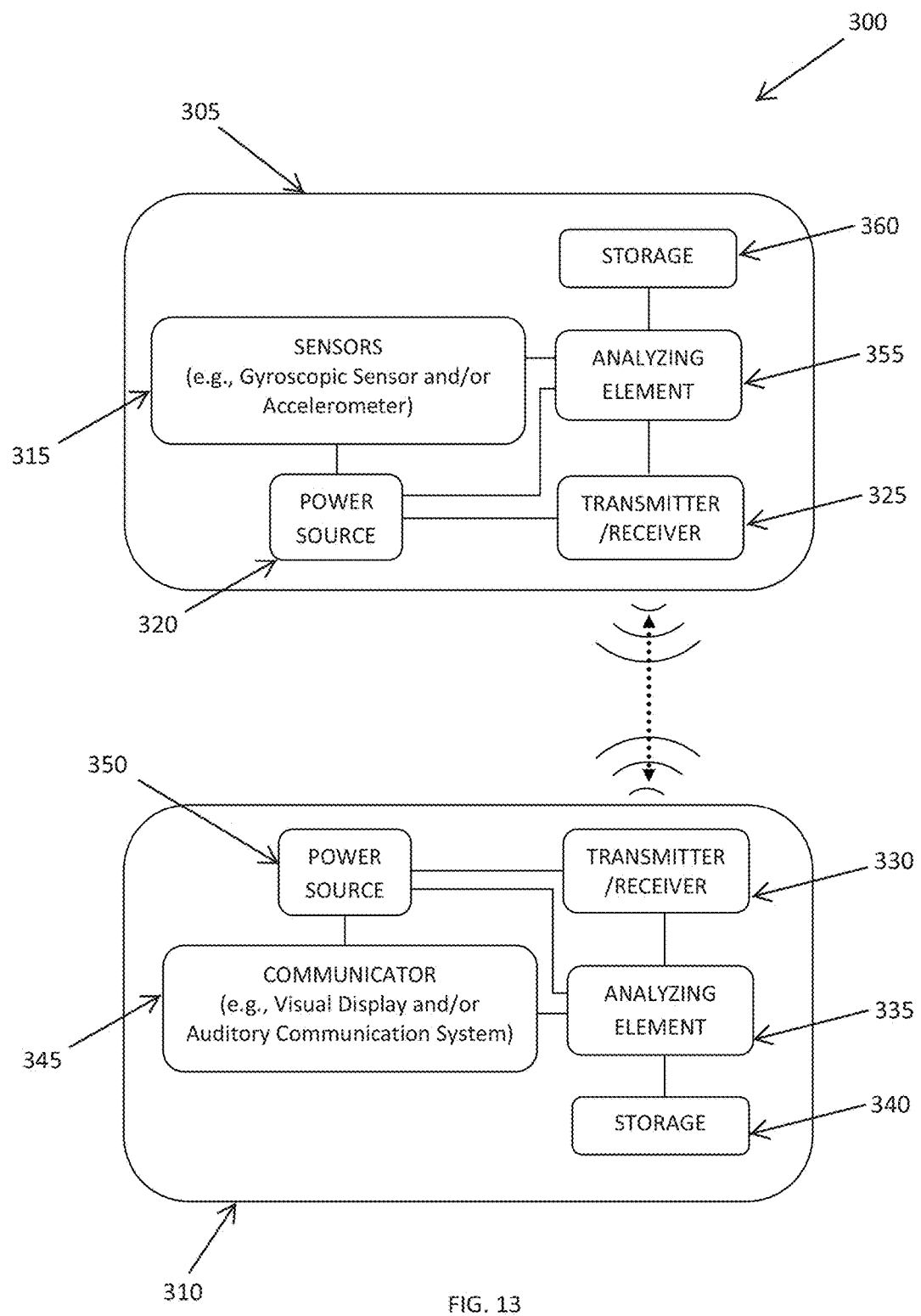
FIG. 13 is a schematic view of another system for providing biofeedback information for an athlete, in accordance with one embodiment of the invention.

Another example system 300 for providing biofeedback information is shown in FIG. 13. In this embodiment, the sensing unit 305 additionally includes an analyzing element 355 and a storage unit 360. Including an analyzing element 355 and a storage unit 360 in the sensing unit 305 allows for initial processing of the raw data from the one or more sensors 315 to be carried out in the sensing unit 305, with the raw and/or analyzed data stored in the storage 360 within the sensing unit 305. As a result, only the processed data, or a small package of information representative of the processed data, need be transmitted from the sensing unit 305 to the remote user feedback element 355, thereby reducing the quantity of information that needs to be transmitted between devices in order to provide real-time feedback to a user. This in turn reduces the drain on the power sources 320, 350, thereby extending the run-time and efficiency of the system 300. In addition, storing raw and/or processed data within the sensing unit 305 allows the data to be downloaded into an analyzing device (e.g., a computer) for further processing after the run is completed, regardless of whether the data was received by a remote user feedback element 355 during the run.

The remote receiving unit 310 may, for example, be a watch, a portable media player (such as, but not limited to, an Apple Inc. iPod®), a customized receiving unit adapted to be worn by the user (e.g., attached to a detachable strap or adapted to fit in a pocket of the user's garments), a mobile phone or smart phone (such as, but not limited to, an Apple Inc. iPhone® or a Research In Motion Ltd. Blackberry®), a portable GPS device, an earpiece, and/or an item of headgear (e.g., a hat, visor, sunglasses, etc). Alternatively, or in addition, the remote receiver may be a laptop computer, a tablet computer, a desktop personal computer, and/or an athletic training system (e.g., a treadmill). In one embodiment the transmitting/receiving element 330 can be a separate unit (for example, a dongle—i.e., a hardware or software "key" allowing two remote devices to communicate) that is adapted to plug into a smart phone or computer to allow communication between the sensing unit 305 and receiving/analyzing unit 310.

The biofeedback information could be communicated to the runner through an auditory, optical, and/or tactile (e.g., vibratory) signal. Auditory signals can, for example, be communicated through a speaker (e.g., a small speaker within the shoe, the sensing unit, and/or receiving device) and/or in an earpiece or headphones worn by the athlete. Optical signals can, for example, be communicated through a visual display on a receiving device (e.g., a visual display on a smart phone screen) or through one or more optical transmitters such as, but not limited to, a light-emitting diode (LED) light source, coupled to the runners shoe and/or to an optical transmitter attached to a piece of apparel or strap worn by the runner. Vibratory signals may be communicated to the runner through a vibration inducing element within the receiver and/or within or attached to the shoe.

The biofeedback information generated through analysis of the measured data from the sensor(s) can be relayed back to the athlete either in any appropriate auditory form such as, but not limited to, a voice command and/or a warning signal. For example, the information may be communicated via a software generated spoken communication providing information and/or instructions to a runner (e.g., "You are now running on your heel"; "Your cadence is too low"; etc). Alternatively, or in addition, the auditory signal may include a click, beep, or other simple signal that can provide a runner with a warning if their running form does not meet a certain requirement and/or provide a positive signal if their running form does meet the required parameters. Such simple auditory signals can also be used to provide timing information (similar to a metronome) to give a runner a target cadence during a run. In addition, or alternatively, the auditory signal may include a change in a pitch, or speed of a musical composition being played to a user depending upon the actual cadence of a user with respect to a target cadence). By providing this practically real-time feedback, the athlete is able to make quick adjustments to their gait during the run.

In various embodiments the biofeedback information may be automatically communicated to the athlete, be communicated upon prompting from the runner (e.g., by initiating a communication command in the receiver), and/or be communicated as a summarized report at set periods (e.g., at the end of a set distance or period covered the athlete could receive summarized biofeedback information relating to his/her performance over the last mile covered and/or the entire distance covered—e.g. "You spent 20% of your time on your heel over the last mile").

One embodiment of the invention can include a system having one or more sensors that are placed inside a shoe of a runner to record foot strike. This information is converted to an auditory signal that is made through a small speaker embedded within, or attached to, the shoe of the runner. As a result, in this embodiment a separate receiving/communicating unit would not be needed to provide feedback to the runner.

In addition to, or instead of, providing real-time biofeedback information, the information may be stored by the system for later analysis by the athlete and/or a coach. This information may be used, for example, to provide an athlete with a history of their runs and their performance during each run. In one embodiment the biofeedback system merely stores data from the sensor(s) as simple raw data, with the processing and analysis of the data being performed by a processing unit upon completion of the run by downloading the raw data to the processing unit. This may be advantageous, for example, in minimizing the size, weight, and/or cost of the actual biofeedback system being carried by the athlete during a run, while still allowing for detailed analysis of the data to be communicated to the athlete and/or coach upon completion of the run.

The processed data may also be uploaded to a shared computer drive or a storage drive (e.g., a cloud computing system) for an online community, thereby allowing the information, or portions thereof, to be reviewed remotely by a coach and/or fellow athlete. In one embodiment, processing and analysis of the data transmitted from the sensors can be carried out by one or more application software programs ("Apps") that may be downloaded onto a smart phone or other electronic device. Such "Apps" can be programmed to analyze data and present biofeedback information in any appropriate way, depending upon the specific training requirements of an athlete.

Figure 14:
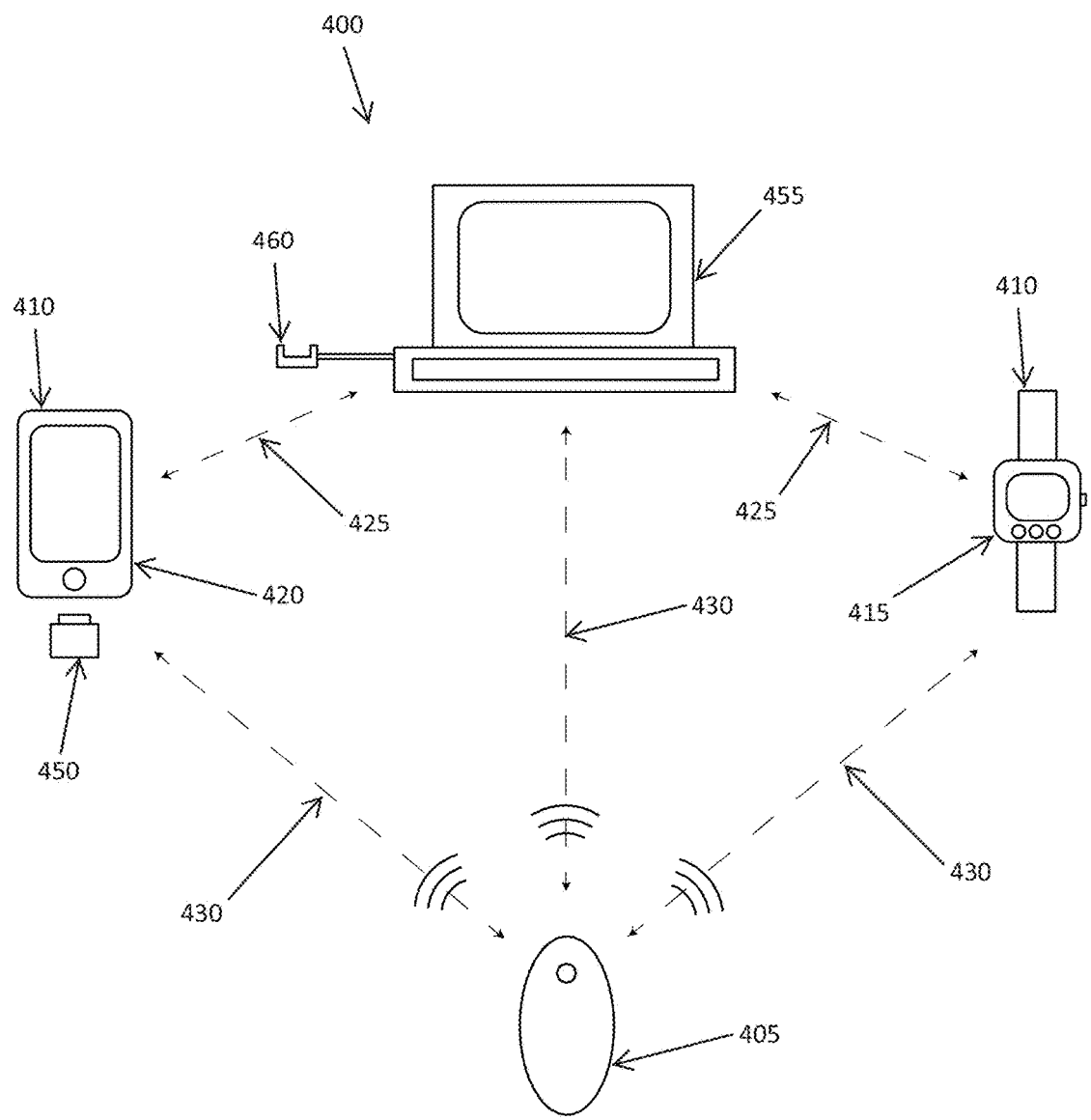
FIG. 14 is a schematic view of yet another system for providing biofeedback information for an athlete, in accordance with one embodiment of the invention.

An example system 400 for monitoring one or more athletic performance characteristic of a user, providing real-time biofeedback information relating to the performance characteristic(s), and/or downloading data associated with the performance characteristic to a computer 455 is shown in FIG. 14. In this embodiment, a sensing unit 405 is adapted to be releasably or fixedly attached to a body portion of a user and, for example, a shoe of a user. The sensing unit 405 can include one or more sensing elements (e.g., a gyroscopic sensor, an accelerometer, etc) for monitoring one or more athletic performance characteristics of the user during an athletic activity such as running. The sensing unit 405 can also include elements such as, but not limited to, one or more power sources (e.g., a rechargeable or replaceable battery), a processing/analyzing unit (e.g., a microprocessor), a memory, an RF transmitting and/or receiving unit, and/or one or more dock contacts 460 for allowing the sensing unit 405 to dock with another device. Docking with another device may, for example, allow for the transferring of measured data (raw and/or processed) from the sensing unit 405 to an analyzing device (e.g., a computer), the transmission of software applications, instructions, upgrades, or settings (e.g., firmware pushes) to the sensing unit 405 from the analyzing device, and/or the recharging of the power source of the sensing unit 405. The dock contacts 460 may include a USB port or other appropriate port for connecting the sensing unit 405 to a receiving/analyzing device.

Data related to the one or more performance characteristics can be transmitted 430 from the sensing unit 405 to one or more remote real-time feedback (RTF) receiving devices 410 and/or to a remote analyzing and storing device 455 (e.g., a computer) for later analysis and long-term storage. The RTF unit 410 may be any of the devices described herein. FIG. 14 shows a system wherein a smart phone 420 and/or a watch 415 can be used to provide real-time feedback to the user. The data associated with the performance characteristic(s) of the user can be transmitted through any appropriate RF signal such as, but not limited to, Bluetooth®, Bluetooth® Low Energy, and/or ANT or ANT+ protocols. In one embodiment the RTF 410 (e.g., the smart phone 420) can communicate directly with the sensing unit 405 without the need for any additional hardware or software. In an alternative embodiment, a dongle 450 may be used to facilitate communication between the RTF 410 and the sensing unit 405.

In one embodiment, the RTF 410 can receive and analyze information from one or more sensing unit 405 and receive and analyze data from other sensors or sources in addition to the sensing unit 405 (e.g., one or more sensors embedded within or directly attached to the RTF 410 and/or one or more additional remote sensor units communicating wirelessly with the RTF 410), thereby allowing for the simultaneous processing of information associated with multiple performance characteristics of the user. For example, the RTF 410 can include, or can communicate with, performance measuring devices such as heart-rate monitors, GPS monitors, speed/distance/time monitors, oxygen level monitors, breathing rate monitors, energy usage monitors, etc.

In various embodiments the RTF 410 can communicate remotely with a computer 455 or other processing/storage device (e.g., a cloud computing system) through a wireless connection, and/or dock with a docking port 460 on the processing/storage device to allow for direct communication therebetween after a run is complete. The RTF 410 may, for example, be adapted to allow for either one or two-way wireless or direct "docked" connection between the RTF 410 and the sensing unit 405, thereby allowing the RTF 410 to download software application, instructions, upgrades, or settings to the sensing unit 405 and/or upload raw and/or processed data from the sensing unit 405 after a run is complete. For example, the sensing unit 405 can send small data packages representative of the performance characteristic (e.g., a foot strike location of a user) to the RTF 410 wirelessly during a run, with the raw data being stored on the sensing unit 405 and downloaded to the RTF 410 and/or to a remote analyzing receiving device 455 through a physical wired connection for further processing after the user's run is complete. The raw and/or processed data can then be stored in the RTF 410 and/or communicated 425 to an analyzing/storage device 455 or facility from the RTF 410.

In one embodiment, a software application ("App") can be provided to an RTF 410 (e.g., a smart phone 420) to control various functions of the RTF 410 and facilitate the receiving of performance characteristic information from the sensing unit 405 and the communication of the associate performance information to the user.

The RTF 410 device (e.g., the smart phone 410 or the watch 415) can communicate information to the user in a variety of ways including, but not limited to, through a visual display screen, through audio signals emitted directly from the RTF 410 or communicated to the user though a wired or wireless (e.g., Bluetooth®) headphone connection, and/or through a vibration emitted by the RTF 410. Such information can be communicated constantly in real-time or at selected intervals. In one embodiment foot strike location information (e.g., a heel strike, a midfoot strike, or a forefoot strike) is communicated to the user, while additional performance characteristics information (e.g., cadence, heart rate, speed, distance travelled, time, etc) can be communicated at the same time, or substantially at the same time, as the foot strike information, or be communicated independently from the foot strike information.

The sensing unit 405 and RTF 410 may be attached to the user in various manners, depending upon the particular performance characteristics being monitored, the particular RTF 410 being used, and the particular real-time feedback being provided to the user. For example, one or more RTFs 410 can be mounted to a wrist, arm, waist, hip, shoulder, head, chest, or leg of a user 435, or be placed in a pocket of a garment of the user 435 or in a bag carried by the user 435. Example configurations of sensing unit 405 and RTF 410 can be seen in FIGS. 15-19. In FIGS. 15-19 the sensing unit 405 is mounted on a fastening portion of the shoe (e.g., releasably attached to the laces of a laced shoe). The biofeedback system 400 may utilize a single sensing unit 405 attached to only one foot of a user, as shown in FIGS. 15-16 and 18-19, or utilize sensing units 405 attached to both feet of the user, as shown in FIG. 17.

Using a sensing unit 405 on both feet allows the system 400 to accurately monitor performance characteristics such as foot strike location on both feet during a run. However, as running gait is often reasonably symmetric (i.e., it is rare for a runner to heel-strike with one foot while midfoot striking with the other foot), valuable training information and biofeedback can be obtained from the use of only one sensing unit pod 405, with the user able to switch the foot on which the sensing unit 405 is mounted between runs (or even during a break in a run) to ensure that feedback relating to the foot strike location on both feet can be provided over time. In addition, additional performance characteristics such as cadence can be obtained through use of only a single sensing unit 405 (as the cadence will be related to twice the number of foot strikes recorded by the sensing unit 405 on only one foot).

Figure 15:
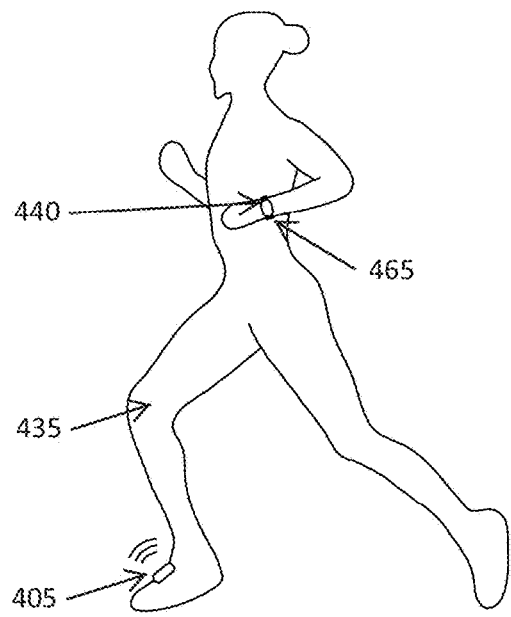
FIGS. 15 to 19 are schematic views of various biofeedback systems as worn by a runner, in accordance with one embodiment of the invention.

In the embodiment of FIG. 15, the RTF 410 is a wrist-based device 465 (e.g., a watch 415 or other appropriate RTF device such as a custom device specifically adapted to receiving information from the sensing unit 405 and communicating that information to a user) strapped to a wrist of the user 435 by a releasable strap or band 440. The wrist-based device 465 can include a visual display to provide a visual indication of the information, include a tactile device to provide a tactile sensation (e.g., a vibration) to the wrist if an event (e.g., a heel strike) occurs, and/or include a speaker to provide an auditory signal if an event (e.g., a heel strike) occurs.

Figure 16:
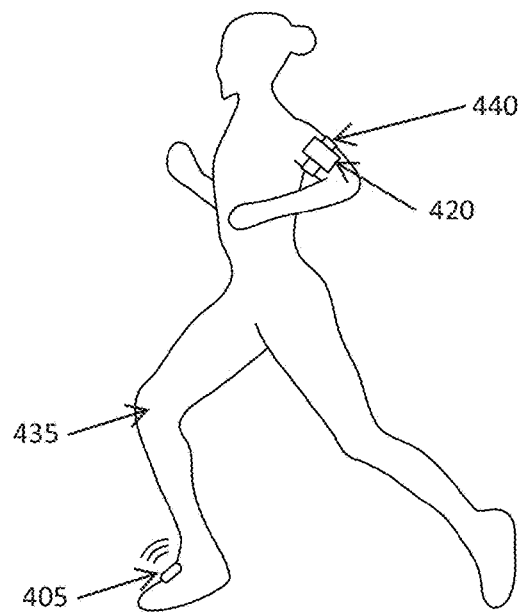
Figure 17:
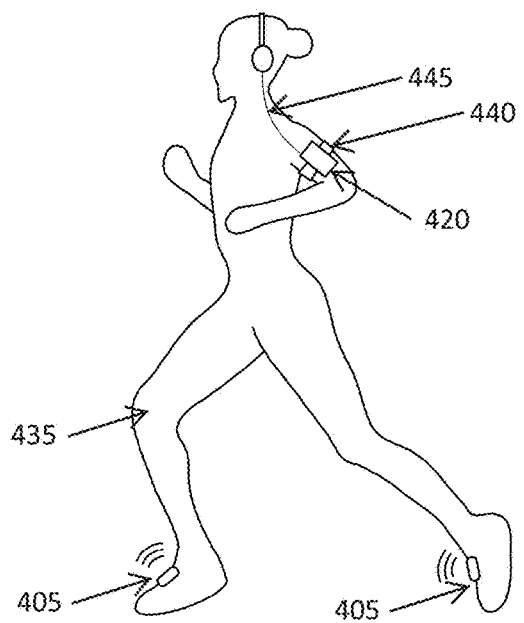

The embodiment of FIG. 16 uses a smart phone 420 including a software application for controlling functionality of the smart phone 420 to allow it to act as an RTF 410. The smart phone 420 is releasably attached to the upper arm of the user 435 by a strap or band 440. As with the watch 415, the smart phone 420 can communicate information to the user 435 through a visual display, a vibration, and/or an auditory signal. For example, the smart phone 420 may output an auditory signal that may be communicated to a user 435 through a pair of headphones 445, as shown in FIG. 17. Utilizing an RTF 410 having two-way communication functionality (such as, but not limited to, a smart phone 420) allows the RIF 410 to both receive information from the sensing unit 405 and transmit information to another remote device (e.g., a computer 455) and/or back to the sensing unit 405.

Figure 18:
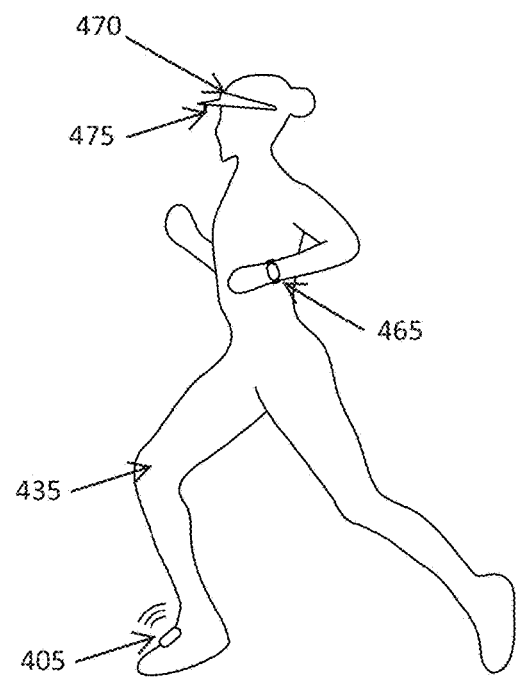

In various embodiments other devices or garments may be used as an RTF 410 for receiving information from the sensing unit 405 and communicating information to the user 435. In the embodiment of FIG. 18, for example, a user 435 may wear a visor 470 that has a receiving element embedded therein or attached thereto. The receiving element may then process the data, if necessary, and communicate information to the user 435 through a visual display element 475 mounted to the visor 470. The visor can also include an auditory feedback element (e.g., a speaker or a headphone connection) and/or a vibratory feedback element in addition to, or instead of, the visual display 475.

Figure 19:
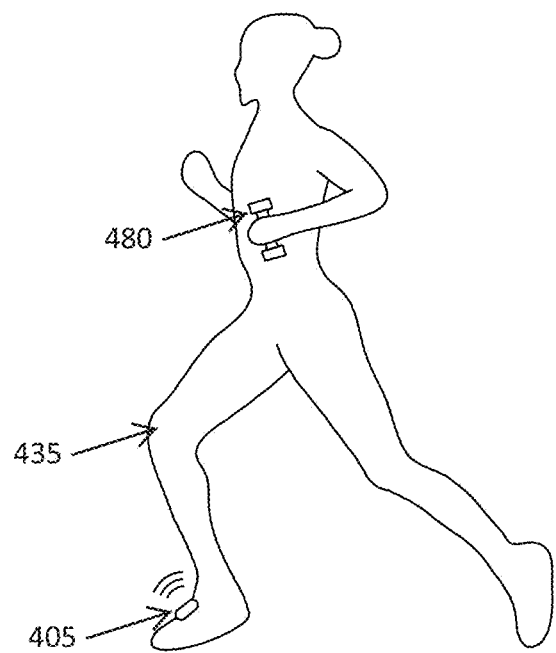
Figure 20:
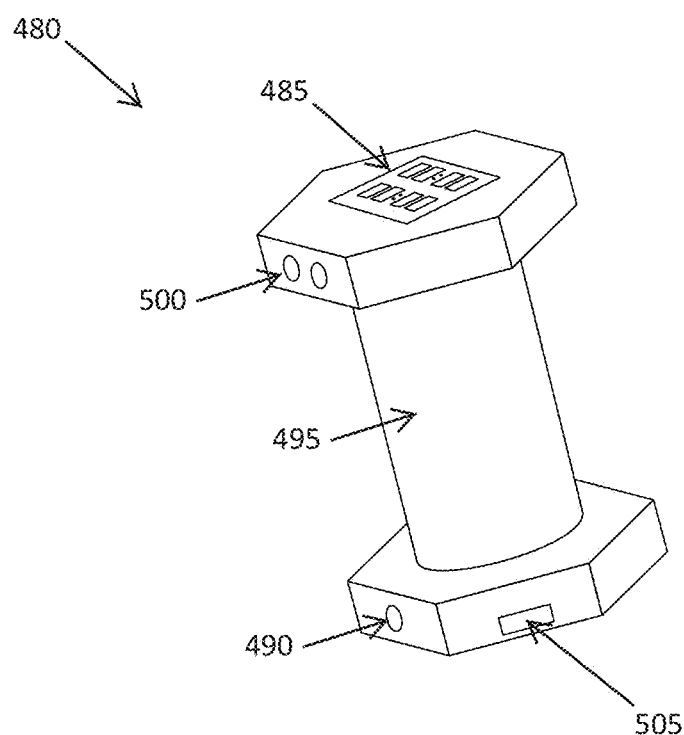
FIG. 20 is a schematic perspective view of a hand held feedback device for a biofeedback system, in accordance with one embodiment of the invention.

In the embodiment of FIG. 19, the RTF 410 may include, or consist essentially of, a hand-held device 480, which can be held in a hand of a user 435 during a run. An example hand-held device 480 is shown in FIG. 20. As with other RTFs 410, the hand-held device 480 can include a variety features such as, but not limited to, user communication elements, controls, and communication ports. As shown in FIG. 20, the hand-held device 480 can include a visual display screen 485 to provide visual information to the user 435, a headphone jack 490 to allow for auditory signals to be sent to the user 435, and a handle 495 having a vibration element held therein to provide tactile feedback to the user 435. Alternatively, or in addition, the hand-held device 480 can include one or more speakers to communicate an auditory signal to the user 435 without the need for headphones. The hand-held device 480 can also include control buttons 500 to allow the user to control one or more function of the hand-held device 480 and one or more communication ports 505 (e.g., a USB port) to allow for the downloading and uploading of information between the hand-held device 480 and another device e.g., a computer 455), and to provide a charging port for the hand-held device 480.

In one embodiment the sensing unit 405 includes a gyroscopic sensor that is adapted to measure an angular velocity of the shoe during athletic activity. Analysis of this angular velocity data can then be used to determine foot strike information relating to the user's running style, thereby allowing the user to be informed of whether a particular foot strike was a heel strike, a midfoot strike, or a forefoot strike. This information can be communicated to the user in rear time, at set intervals, and/or be stored in the sensing unit 405 for later analysis and processing. In addition, data from a gyroscopic sensor can be used to determine when a foot strike occurs, thereby allowing for the measurement of cadence (i.e., number of foot strikes per minute) information for the user. For example, foot strike location information (e.g., a heel strike, a midfoot strike, or a forefoot strike), cadence information, and/or other performance characteristic information can be communicated to the user upon every foot strike. Alternatively, or in addition, compiled and/or averaged performance characteristic information can be communicated to the user upon the completion of a preset or user selected number of foot strikes, upon the completion of a preset or user selected distance travelled or time travelled, upon request from the user, and/or at the end of a run.

Figure 21:
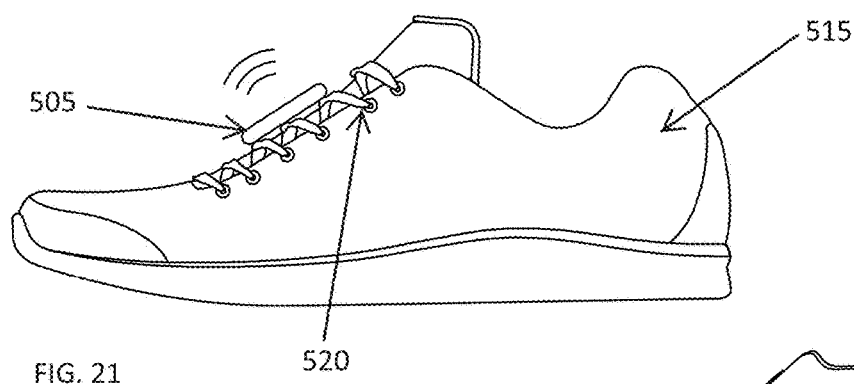
FIG. 21 is a schematic side view of a sensor pod for a biofeedback system positioned on a lacing portion of a shoe, in accordance with one embodiment of the invention.
Figure 22:
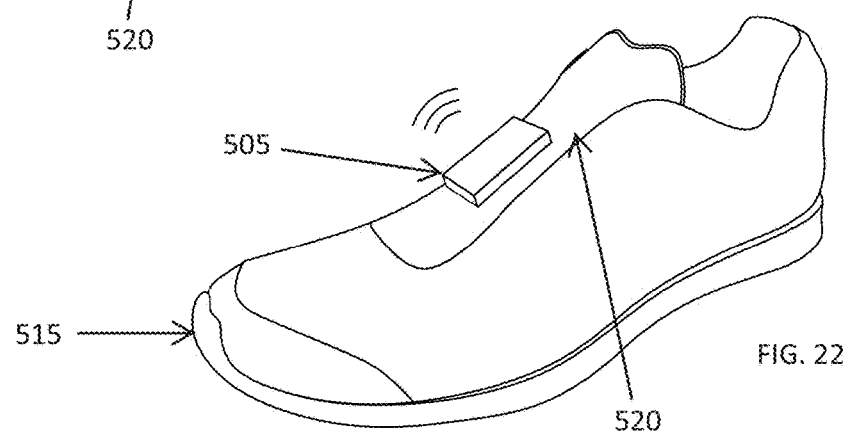
FIG. 22 is a perspective view of the pod of FIG. 21.
Figure 23:
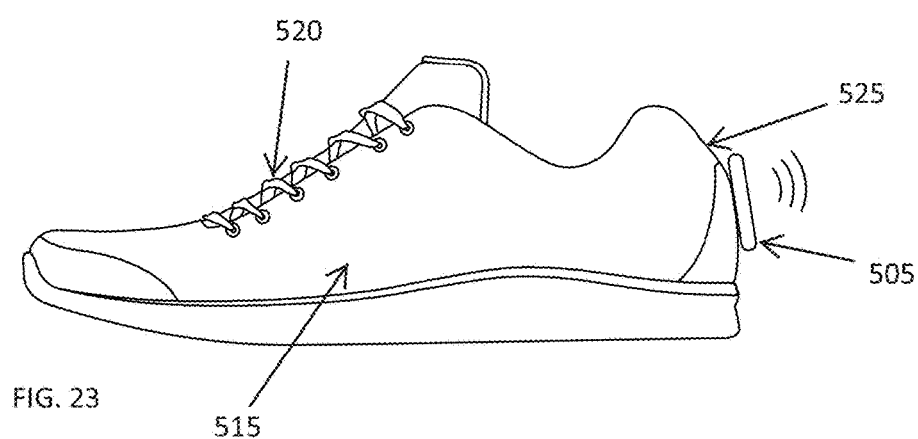
FIG. 23 is a schematic side view of a sensor pod for a biofeedback system positioned on a heel portion of a shoe, in accordance with one embodiment of the invention.
Figure 24:
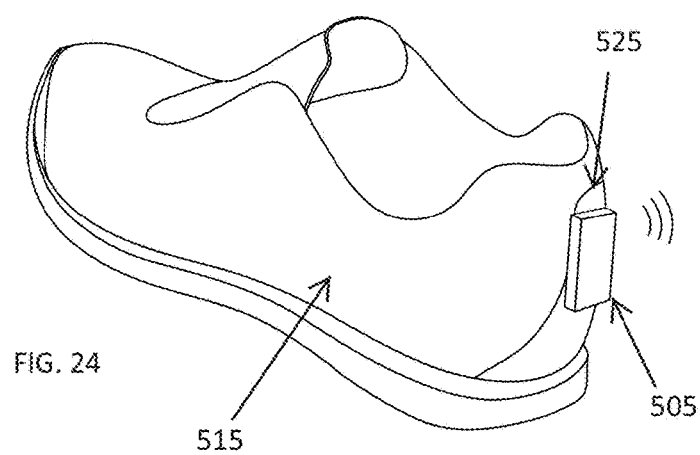
FIG. 24 is a perspective view of the pod of FIG. 23.

In one embodiment, a sensing unit including a gyroscopic sensor can be releasably mounted to an upper of a shoe at a fastening portion (such as a lacing portion or hook-and-loop fastening portion) located centrally, or substantially centrally, on the top of the shoe. An example gyroscopic sensor unit 510 mounted to the lacing portion 520 of a shoe 515 is shown in FIGS. 21 and 22. Alternatively, the gyroscopic sensor unit 510 can be mounted to a heel portion 525 of a shoe 515, as shown in FIGS. 23 and 24, or to any other appropriate location on the upper or sole of the shoe 515, depending upon the shoe, the specific mounting arrangement required, and/or the measurement and calibration requirements of the sensor.

Figure 25:
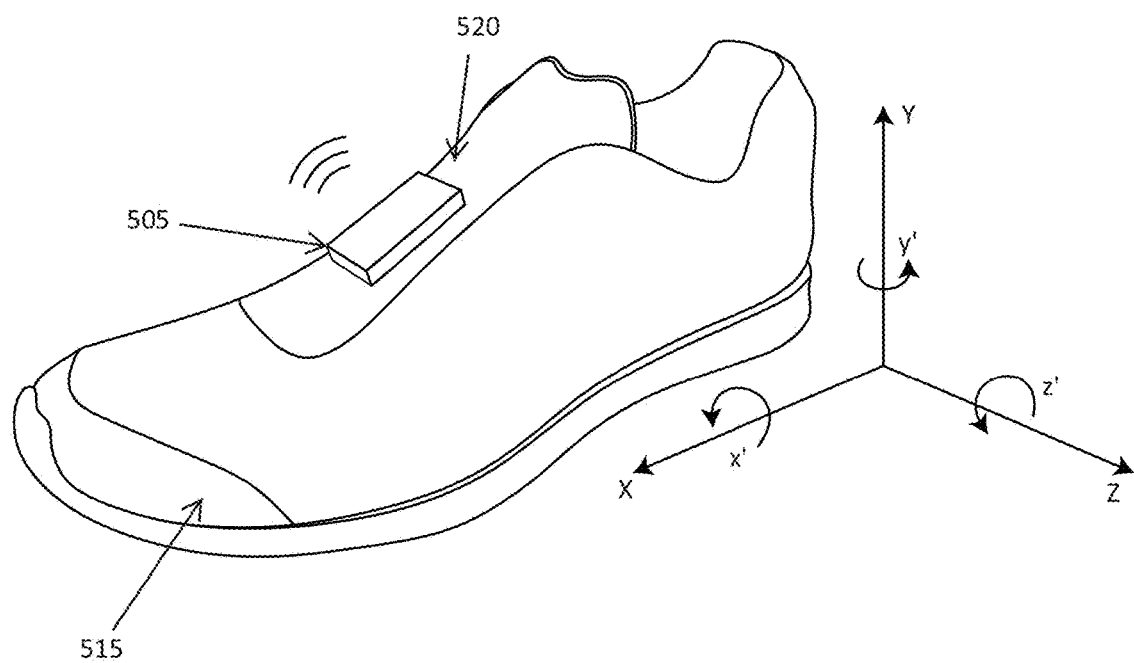
FIG. 25 is a schematic perspective view of axes of orientation for a gyroscopic sensor for a biofeedback system, in accordance with one embodiment of the invention.

The gyroscopic sensor may be a one-axis sensor, a two-axis sensor, or even a three-axis sensor, allowing for the measurement of angular velocity (x', y', z') about any axis (X,Y,Z), as shown in FIG. 25, and thereby allowing for the measurement of a variety of performance parameters associate with a foot strike. For example, careful analysis of an angular velocity measurement z' about the Z-axis allows for the identification of a foot strike location (i.e., a heel strike, a midfoot strike, or a forefoot strike) of a user during a stride, and thereby also provides information as to whether a user's foot is dorsiflexed (heel strike), plantarflexed (forefoot strike), or neutral (midfoot strike) upon impact with a ground surface. Similarly, careful analysis of an angular velocity measurement x' about the X-axis allows the system to identify whether a user's foot is pronating (wherein the ankle caves inwards towards the other foot) or supinating (wherein the ankle caves outwards away from the other foot) at impact with a ground surface. In addition, analysis of an angular velocity measurement y' about the Y-axis allows the system to identify whether a user's foot is abducting (wherein the forefoot rotates outwards away from the other foot) or adducting (wherein the forefoot rotates inwards towards the other foot) at impact with a ground surface.

In general, the goal of an algorithm processing raw z' angular velocity data from the gyroscopic sensor(s) is to accurately detect the direction and speed of the foot's rotation at the moment of impact with a ground surface, and to determine from this the type of foot strike (i.e., forefoot, midfoot, or heel strike) and the severity of the foot strike (e.g., severe heel strike, intermediate heel strike, mild heel strike, midfoot strike at rear of midfoot, midfoot strike at center of midfoot, midfoot strike at front of midfoot, mild forefoot strike, intermediate forefoot strike, or sever forefoot strike). An example method of calculating foot strike location information from a gyroscopic sensor reading is discussed below. In this embodiment, only data from one single-axis of a gyroscopic sensor is required to measure foot strike location and cadence.

The data recorded from the gyroscopic sensor may be considered to be periodic, with each gait cycle being one period. During a normal gait cycle, the foot often has a positive rotation just before the foot strike (see, for example, FIGS. 26 and 27). After the foot strike, during the stance phase of the gait, the foot is flat on the ground and is relatively motionless. The foot strike occurs during a short time period (e.g., between about 10 ms to 50 ms and, for example, about 30 ms or so) between the end of the swing phase and the start of the stance phase, with the angular velocity data (z') about the Z-axis during that period providing information that can be analyzed to determine the type of foot strike.

During a heel striking event the heel touches the ground first, followed by a rapid rotation of the foot forwards until the sole is flat against the ground. As a result, a large positive rotational velocity during a foot strike event, accompanied by little or no negative rotational velocity, is measured for a heel strike. In contrast, midfoot striking is indicated by a smaller positive rotational velocity followed by a clearly defined negative rotational velocity, while a forefoot strike shows a larger negative velocity than that observed for a midfoot strike. Thus, there is a clear qualitative difference in the gyroscopic sensor data about the Z-axis between heel striking and forefoot/midfoot striking. It is often found that the maximum localized rotational velocity occurs close to, but slightly after, the initial impact during a foot strike event.

In one embodiment, raw data from the gyroscopic sensor can be analyzed to determine foot strike location for a foot strike event. In an alternative embodiment, pre-processing of the data (for example through amplification and/or low-pass, high-pass, band-pass, band-stop, and/or butterworth filtering) may be carried out prior to analyzing the data to determine foot strike information. The sample rate of the gyroscopic sensor can also be set at any appropriate rate to ensure that the sample rate is sufficient to obtain accurate information without sampling at a rate that would draw too much power and/or take up too much storage space. The sample rate may be set, for example, at between 500 to 5000 Hz or between 500 and 2000 Hz or, more particularly, between 800 and 1500 Hz and, for example, at about 900 Hz. In one embodiment, a sample rate of about 900 Hz may be set to ensure that at least about 300 samples are taken per stride.

Figure 26:
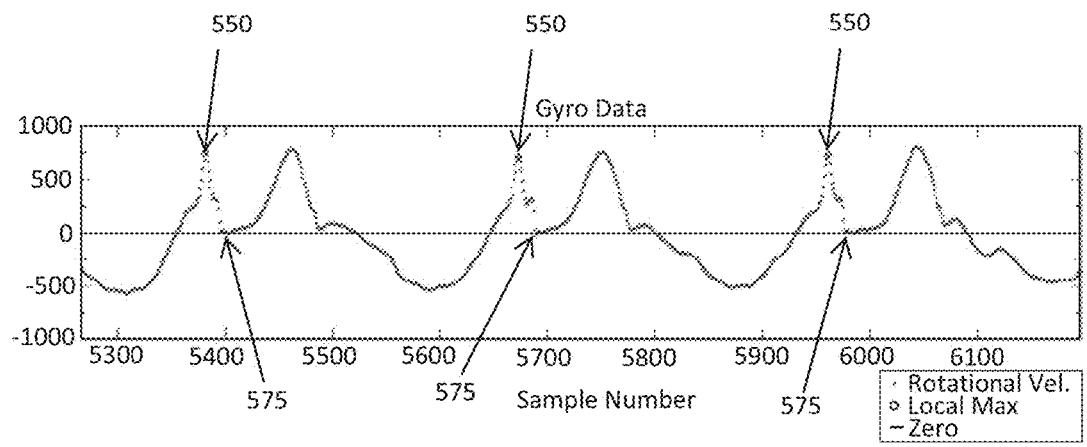
FIG. 26 is a graph of angular velocity data from a gyroscopic sensor for a heel striking running style, in accordance with one embodiment of the invention.
Figure 27:
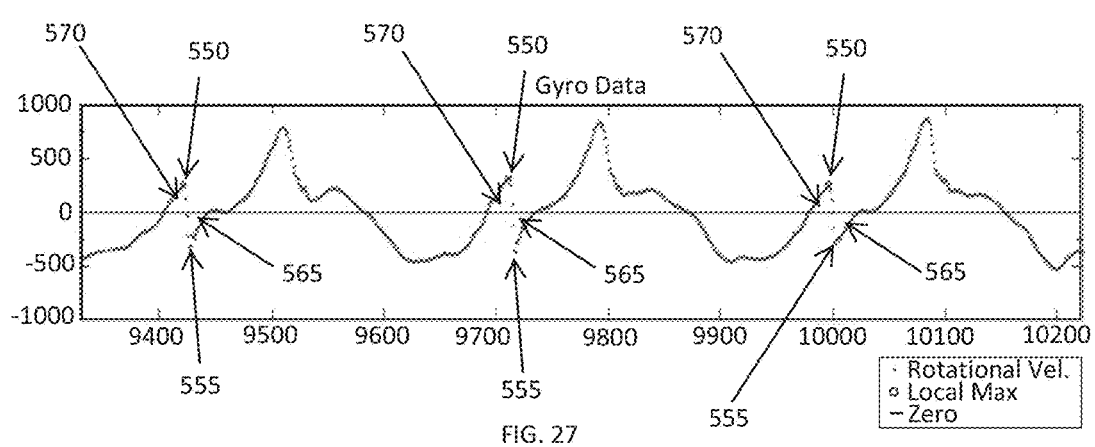
FIG. 27 is a graph of angular velocity data from a gyroscopic sensor for a midfoot striking running style, in accordance with one embodiment of the invention.

Example gyroscopic sensor data for a heel strike is shown in FIG. 26, while example raw gyroscopic sensor data for a midfoot strike is shown in FIG. 27. Three foot strike events are shown in each graph. As shown, the midfoot strike exhibits a positive spike 550 followed by a negative spike 555, with the negative component showing that the foot is rotating "backwards" (i.e., the heel is coming down relative to the toe) after initial impact. Conversely, the heel strike has a positive spike 550 but does not have a negative component (i.e., the local minimum 575 is never less than zero), showing that the foot is rotating "forwards" (i.e., the toe is moving down relative to the heel). A forefoot strike is characterized by having a small positive peak 550 relative to the negative peak 555, showing that the foot is rotating backwards more severely than for a midfoot strike. Cadence can be determined simply by counting the number of foot strike events over a specified time.

Figure 28:
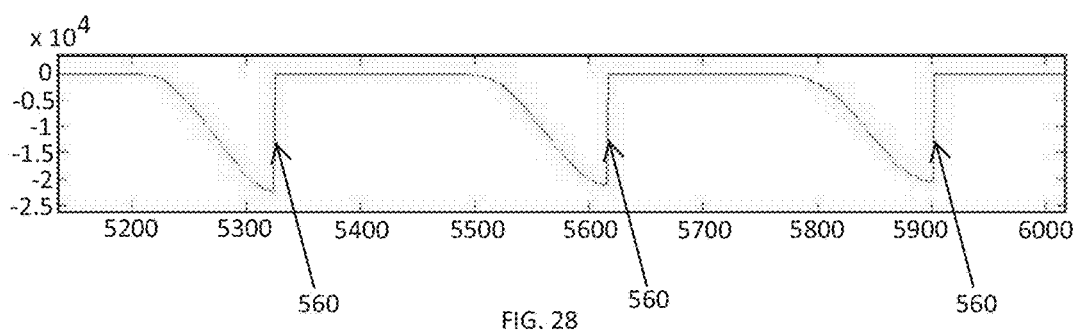
FIG. 28 is a graph of data for a reset trigger for a gyroscopic sensor, in accordance with one embodiment of the invention.

In one embodiment, a microprocessor analyzes each angular velocity sample from the gyroscopic sensor and determines whether or not a foot strike has occurred. To find the moment of foot strike, the microprocessor first needs to distinguish one stride from another with a periodic trigger, as shown in FIG. 28. When the foot is swinging forward, the toe is moving up and the rotational velocity is negative. When the rotational velocity is negative, the microprocessor adds each sample to a sum. When the sum reaches a preset level, a flag is set and the sum resets 560. This happens once for each stride, just before the moment of the foot strike. After the flag is set, the microprocessor starts looking for a maximum value 550. Once found, it finds the minimum value 555 within a set window. It is the ratio of this maximum and minimum value that determines the rating for the foot strike.

The window during which the maximum and minimum angular velocity measurements are taken for the foot strike location analysis may be set to any appropriate size and starting point to ensure that the required maximum and minimum peaks are captured without additional, non-relevant, data contaminating the calculation. For example, the window may be set to capture and analyze data starting at, and/or ending at, a particular identifying event during the periodic data cycle or a specific time period or specific number of samples prior to or after a particular identifying event during the periodic data cycle, and/or be set to cover a specific time period or a specific number or samples from a set starting point, as appropriate.

In one embodiment the window may begin from the moment of initial impact, or the moment of the first local maximum angular velocity after the initial impact, and continue until a point at or after a first local minimum angular velocity measurement is observed. Alternatively, the window may be set to review data captured within a specific time window (e.g., between 10 ms to 50 ms and, for example, about 30 ms) or sample size starting at the moment of initial impact, or at the moment of the first maximum rotational value peak after initial impact, or at any other appropriate time prior to, at, or after the instant of initial impact. In another embodiment, the window for analysis may open at the time at which the angular velocity is zero prior to initial impact, and close at the time at which the angular velocity transitions from negative to positive after the local minimum angular velocity is observed.

In one embodiment, a determination of the foot strike location can be calculated by comparing the maximum value with the minimum value within the sample window in accordance with the following equation:

Foot strike Location Rating $(F)=|(\text{Local Minimum value}*100)/\text{Local Maximum Value}|$ The results of this calculation produce a non-dimensional value from $F_{min}$ to $F_{max}$ (for example, a value of between $F_{min}=0$ and $F_{max}=100$), with $F_{min}$ indicating a severe heel strike, $F_{max}$ indicating a severe forefoot strike, and values in the middle of the range indicating a midfoot strike. The specific values identifying each range may, for one example user, be:

$X_1$ to $X_2$=heel strike (with "$X_1$" indicating a sever heel strike and values closer to $X_2$ indicating a more mild heel strike)

$X_2$ to $X_3$=midfoot strike $X_3$ to $X_4$=forefoot strike (with "$X_4$" indicating a sever forefoot strike and values closer to $X_3$ indicating a more mild forefoot strike)

The values for $X_3$ and $X_4$ may be either preset or be calibrated and/or selected to ensure accuracy for a specific user. Example ranges for the values of $X_2$ may be about 15-40 or, more particularly, about 20-30 or 20-25 or, more particularly, about 20. Example ranges for the values of $X_3$ may be about 60-80 or, more particularly, about 65-75 or 65-70 or, more particularly, about 70.

Additional processing may be carried out to provide accurate foot strike position information, if appropriate. For example, a Gaussian multiplier or other appropriate $2^{nd}$ order multiplier may be applied to assist in analyzing the results. Additionally, or in the alternative, results outside a set results window (e.g., outside the ranges $F_{min}$ to $F_{max}$) may be either discarded or shifted to a preset default value. For example, any result greater than $F_{max}$ can either be shifted to indicate a value "$F_{max}$" or be discarded entirely.

In an alternative embodiment, a ratio of the integral of the negative portion of the curve 565 against the integral of the positive portion of the curve 570 (i.e., from calculations of the area under the negative portion of the curve 565 and the positive portion of the curve 570) may be utilized to produce the foot strike location rating, rather than ratios of the absolute values of the minimum and maximum local peaks. The data to be integrated may be taken over any appropriate window size. Utilization of integrated results may be useful, for example, in producing accurate readings in situations where the sample rate of the gyroscopic sensor is insufficient to ensure that accurate local maximum and minimum peak values can be obtained. In addition, the integral of rotational velocity relates to a change in angle of the foot, which may produce valuable performance characteristic information relating to the foot strike of a user. Where beneficial, various other embodiments may utilize other appropriate algorithms for processing the data to determine the foot strike information.

In one embodiment, the sensor unit may be set to go into a "sleep-mode" (i.e., a reduced power consumption mode) during periods of inactivity. This sleep-mode may be set to turn on (when a sensor remains at rest for a given period) and off (when the sensor is moved) automatically. Alternatively, or in addition, the sensor unit may include a user interface (e.g., a hardware switch or a software "switch" initiated by a wireless signal from an RTF) allowing a user to turn the power to the sensor on and off manually.

In one embodiment, the gyroscopic sensor takes data continuously throughout entire gait cycle. However, in alternative embodiment, the gyroscopic sensor can be turned on and off during a gait cycle so that it only takes data during the foot strike event phase of the gait cycle. This may, for example, reduce power consumption by the sensor unit and/or reduce the amount of raw data being stored and/or processed by the sensor unit. For example, a separate sensor (e.g., an accelerometer) may be used in the sensor unit in addition to the gyroscopic sensor, with the accelerometer being used to indicate when a foot strike event is taking place and the gyroscopic sensor only capturing angular velocity data upon triggering by the system when the accelerometer data indicates that a foot strike event is occurring. Additionally, or alternatively, the accelerometer data may be used to calculate the cadence information (with the gyroscopic sensor data only being used for foot strike location calculations), and/or the accelerometer may be used to determine whether a user is standing still, walking, or running, with the gyroscopic sensor only being activated when the user is running. The accelerometer can, for example, determine whether a foot strike event is a walking foot strike or running foot strike based on the magnitude of the acceleration measured at impact (with, for example, a running foot strike indicated by a higher magnitude acceleration measurement).

Figure 29:
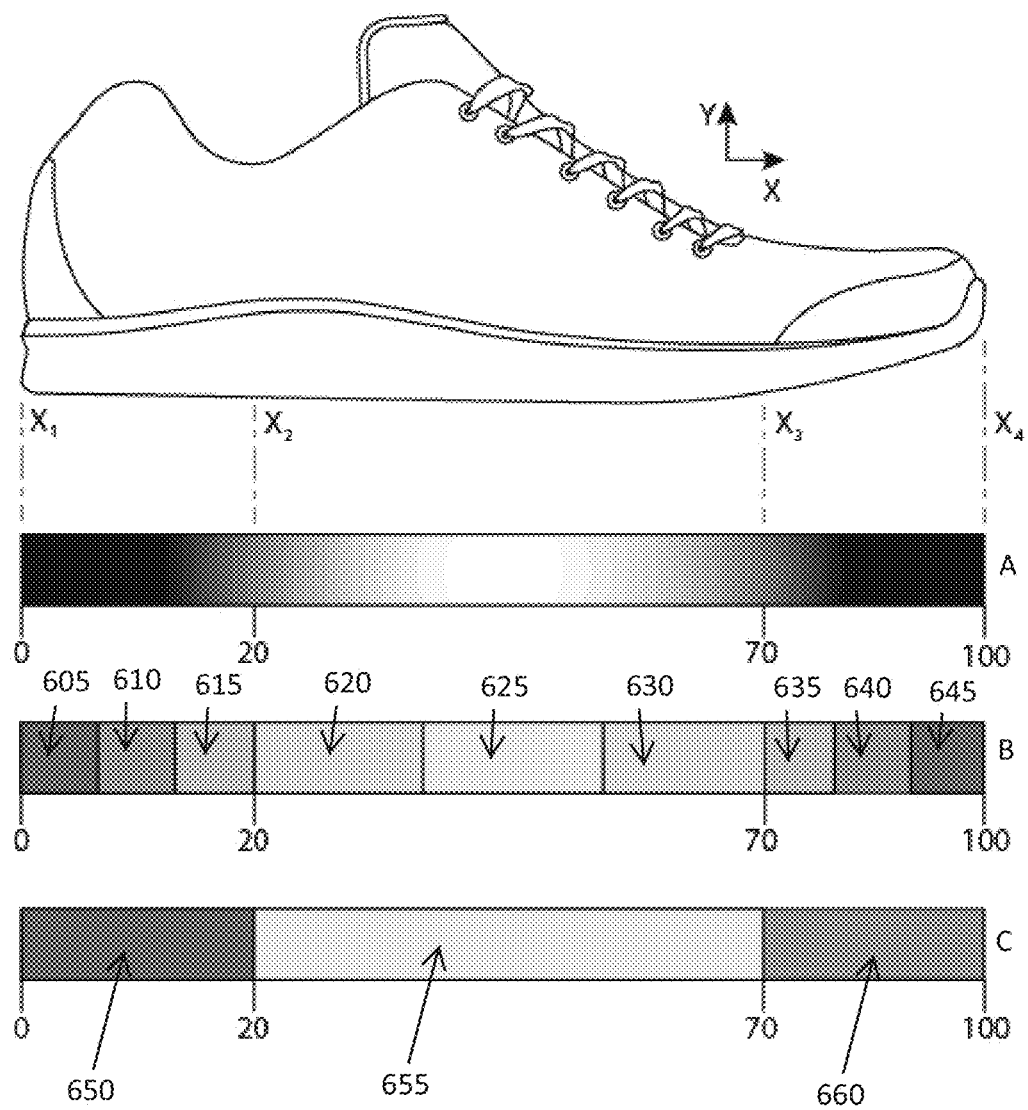
FIG. 29 is a schematic representation of various data presentation means for foot strike location of a runner, in accordance with one embodiment of the invention.

The performance characteristic information (e.g., the foot strike location information) can be processed and communicated to the user in a number of ways. For example, in one embodiment, as shown in FIG. 29(A), the raw data can be processed to produce a foot strike location rating value of between $F_{min}$ and $F_{max}$ (e.g., between 0 and 100), with that value being stored and communicated to the user. In this example, the user would be provided with an accurate calculation of exactly where on the foot the centre of the initial foot strike impact occurred, with a further indication of whether this value represented a heel strike, a midfoot strike, or a forefoot strike being calculated based on the set values for $X_2$ and $X_3$.

In one embodiment, as shown in FIG. 29(B), the foot strike location rating value can be placed into one of a number of "bins", with the system communicating to the user which bin a particular foot strike (or an average foot strike) fell. In the embodiment of FIG. 29(B) the foot strike information is divided into nine bins (severe heel strike 605, intermediate heel strike 610, mild heel strike 615, midfoot strike at rear of midfoot 620, midfoot strike at center of midfoot 625, midfoot strike at front of midfoot 630, mild forefoot strike 635, intermediate forefoot strike 640, or sever forefoot strike 645), although a greater or lesser number of bins may be used where appropriate. In a further alternative embodiment, the foot strike location rating value can be used to merely indicate whether a heel strike 650, a midfoot strike 655, or a forefoot strike 660 has occurred, as shown in FIG. 29(C).

By performing the analysis described hereinabove with a microprocessor within the sensor unit the performance characteristic data transmitted to a receiving unit can be limited to merely a small package or data representing the foot strike location rating value or the appropriate "bin" into which a given value falls. The cadence information can also be transmitted along with the foot strike information, or may be determined inherently from the time at which each foot strike value is transmitted. Minimizing the data that needs to be sent from the sensing unit to the RTF can reduce the power required by the system and thereby extend the running time of the system.

In various embodiments this information may be communicated to the user through a visual signal, an auditory signal, and/or a tactile signal. For example, an RTF could generate a sound (e.g., a buzz), cause a vibration, and/or flash a visual indicator only when a certain event occurs (e.g., a heel strike). Alternatively, different sounds, visual signals, and/or vibrations could be assigned to different events, thereby providing a different indicator to the user depending upon the event occurring. The severity of an event (e.g., a severe, intermediate, or mild heel strike) may be indicated, for example, by different sounds or by changes in the volume, pitch, tone, or other acoustic parameter of a given sound. Similarly, variations in the intensity or color and/or variations in the intensity of a vibration can be used to differentiate between different severities of a given foot strike event. In one embodiment the auditory, visual, and/or tactile signals associated with a specific foot strike position may be preset, or be selected by the user depending upon his/her particular preferences and the functionality of the RTF being used.

The sensing unit can, in one embodiment, include a housing unit adapted to house the sensor, a power source, a processor, and/or a transmitter. The housing unit may, for example, provide a protective casing for the sensor and other electronics and/or provide a mounting means by which the sensor can be mounted to the shoe of the user. The housing unit may be adapted to be releasably attachable to a sole and/or upper of the shoe of the user, or be fixedly attached to, or embedded within an upper and/or sole of the shoe. In one embodiment the housing unit is releasably attachable to at least one of a fastening portion (e.g., the lacing portion or a hook-and-loop fastening portion) of a shoe or a heel portion of the shoe. The housing unit may have an integrated mounting element for mounting the device to a shoe. Alternatively, the housing unit and mounting unit may be separate, attachable, elements that can be coupled together to mount the sensor package to the shoe. Example housing units 700 and mounting elements 705 are shown in FIGS. 30a to 33c.

Figure 30A:
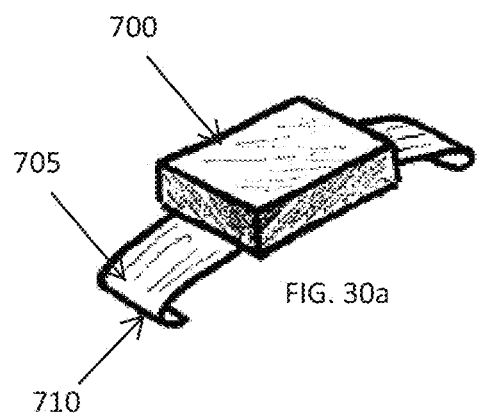
FIGS. 30a to 33c are schematic views of various attachment mechanisms for a sensor pod for a biofeedback system, in accordance with one embodiment of the invention.
Figure 30B:
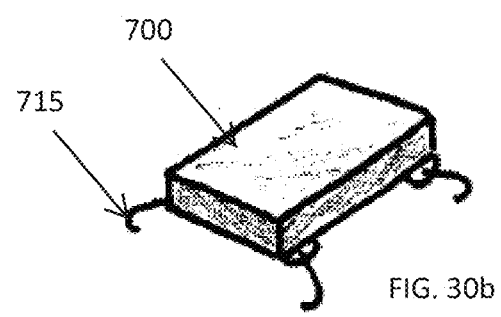
Figure 30C:
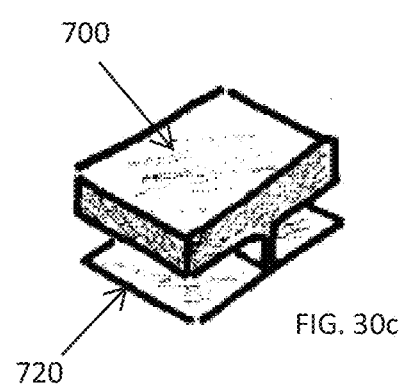

The embodiment shown in FIG. 30a includes a housing unit 700 that is either fixedly or detachably attached to an elastic or inelastic mounting element 705 that includes hooked ends 710 for engaging the laces of a shoe. FIG. 30b includes a housing unit 700 having a plurality of elastic or inelastic hooks 715 extending from the housing unit 700 for engaging the laces or the eyelets of a shoe. FIG. 30c includes a housing unit 700 having a flexible or inflexible base unit 720 that can be placed under the laces of a shoe and be fixedly or detachably connected to the housing unit 700.

Figure 30D:
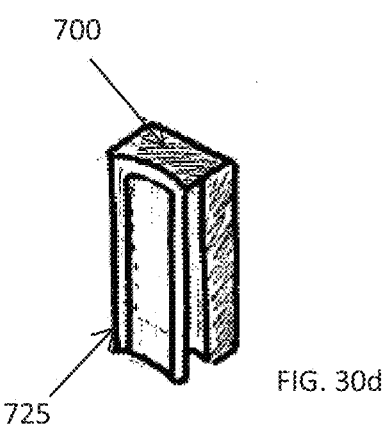
Figure 30E:
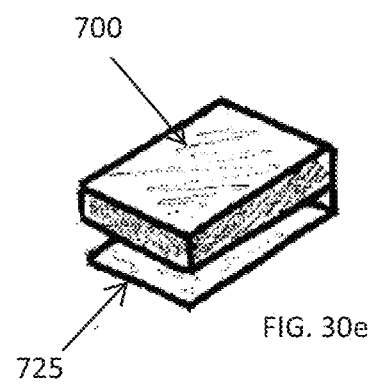
Figure 30F:
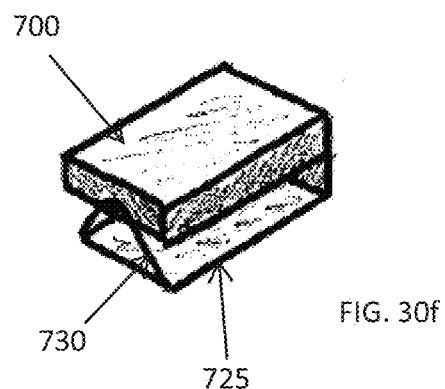
Figure 30G:
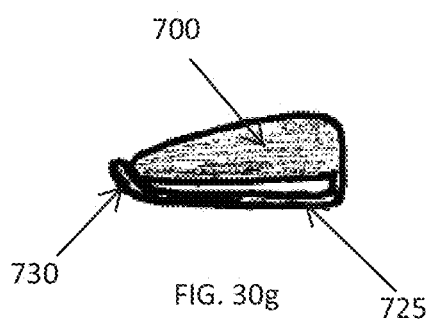

FIGS. 30d and 30e include a flexible or inflexible base unit 725 that can be slid over the heel of a shoe or slid into a pocket on the heel of the shoe (as shown in FIG. 30d), or slid under the laces of a shoe a shown in FIG. 30e). The base unit 725 may include pins for pinning the base unit 725 into one or more layers of the upper the shoe. Again, the base unit 725 can be fixedly or detachably attached to the housing unit 700. FIGS. 30f and 30g show a similar configuration but with a latching element 730 allowing the end of the base unit 725 to latch onto the housing unit 700 to lock it in place when mounted to the shoe.

Figure 31A:
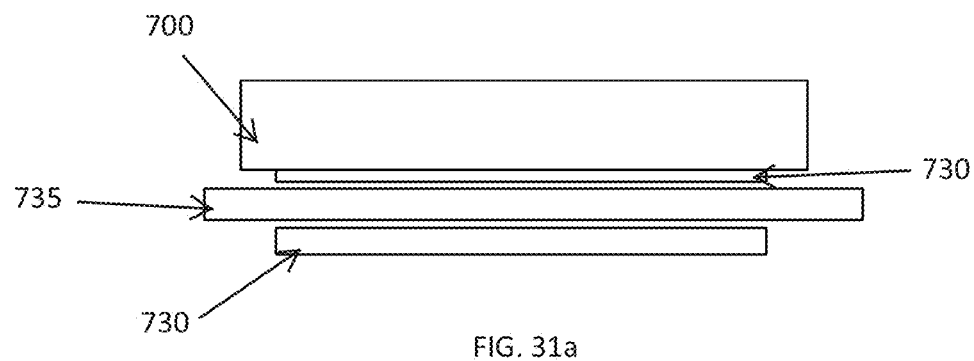
Figure 31B:
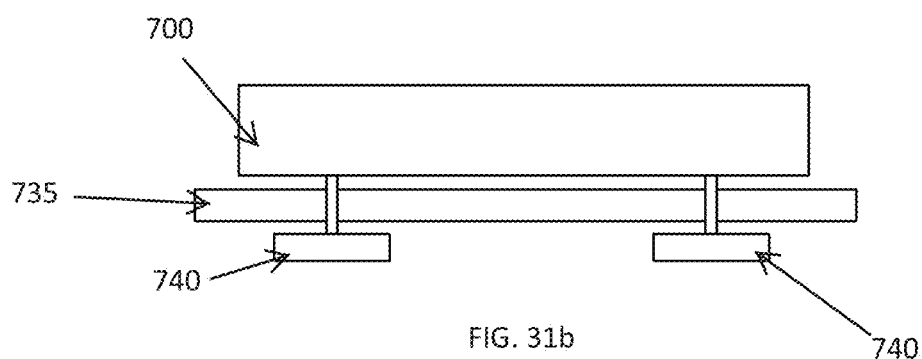
Figure 32A:
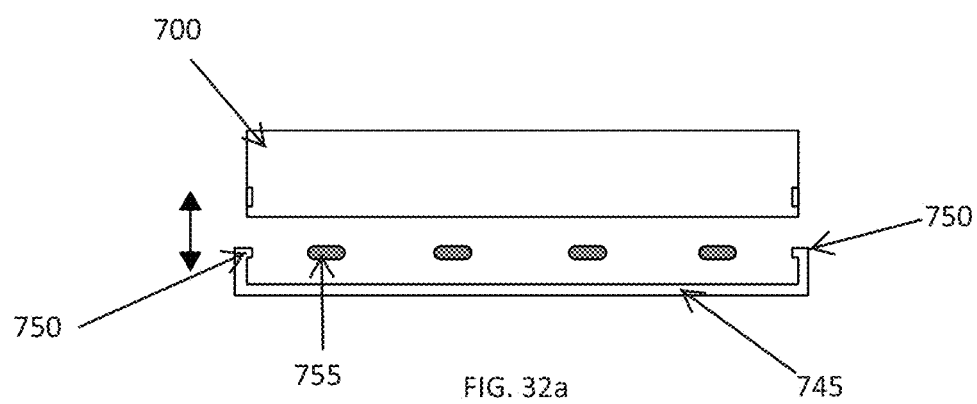
Figure 32B:
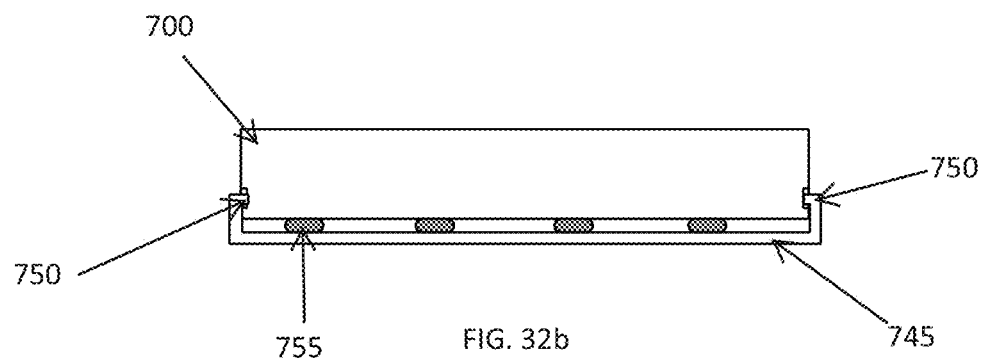

In one embodiment, as shown in FIG. 31a, magnetic elements 730 can be used to releasably attach a housing unit 700 to the upper of a shoe 735, while in FIG. 31b pins 740 may be inserted through the upper of the shoe 735 to releasably or fixedly hold the housing unit 700 thereto. In another embodiment a detachable mounting unit 745 having a plurality of latching elements 750 can be placed below the laces 755 of a shoe, as shown in FIGS. 32a and 32b, thereby allowing the housing unit 700 to be detachably mounted to the lacing portion of the shoe.

Figure 33A:
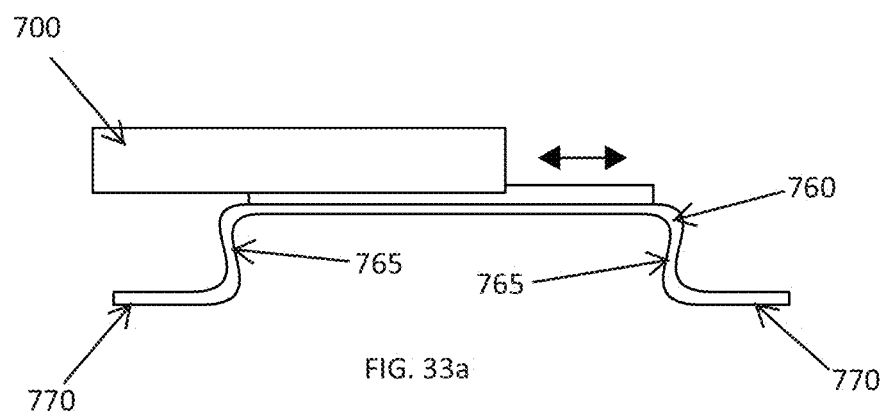
Figure 33B:
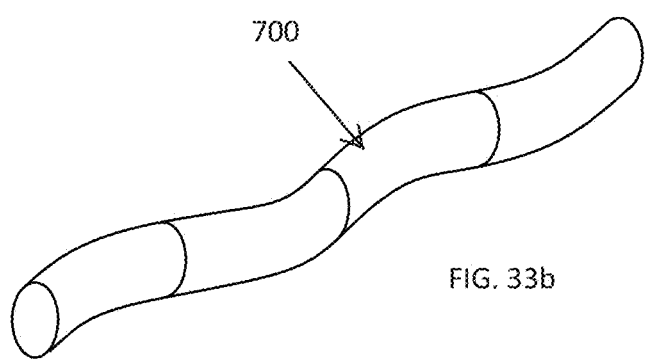
Figure 33C:
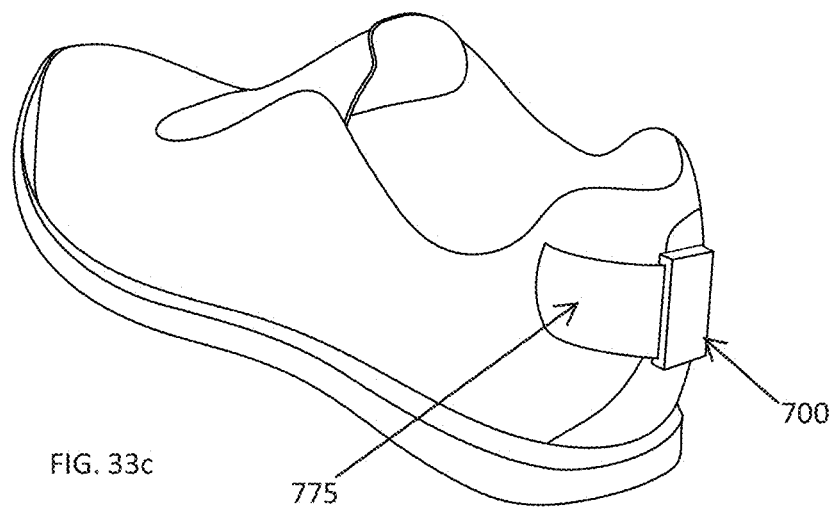

In one embodiment, as shown in FIG. 33a, a housing unit 700 can be slideably connectable with a mounting unit 760. The mounting unit 760 may include flexible arms 765, that can be pinched in to allow the ends 770 of the arms 765 to be hooked under the laces of the shoe or the sides of the lacing portion of the upper of the shoe. The arms 765 may alternatively be fixedly mounted to the housing unit 700. In another embodiment, as shown in FIG. 33b, the housing unit 700 may be formed from a flexible elongate length of material with the sensor, a power source, a processor, and/or a transmitter held within. This flexible housing could, for example, be slid below the laces and held in place by the closing force applied by the laces to the shoe. In yet another embodiment a housing unit 700 may be releasably or fixedly mounted to a clip 775 that can be clipped onto the upper of a shoe at a heel portion (as shown in FIG. 33c) or over a lacing portion of a shoe, or be attached to the upper of a shoe through an adhesive attachment, a hook-and-loop attachment, a pinned attachment, or any other appropriate attachment means.

In one embodiment data from a gyroscopic sensor coupled, for example, to an upper body of a user can be used to provide posture and/or lean information during a run. For example, a gyroscopic sensor in a smart phone or other RTF strapped to the upper body of the user (e.g., on the torso or upper arm of the user) can be used to measure posture and/or lean information that can be coupled with the foot strike and cadence information to provide the runner with a more complete analysis of their running form. The smart phone may then act as both a sensor unit and an RTF. In one embodiment, the user can calibrate the gyroscopic sensor within the smart phone or other RTF prior to use, for example by simply strapping the smart phone to their person and then standing upright (e.g., against a wall) to "zero" the sensor prior to the run.

In one embodiment, the foot strike position information may be supported by GPS data, or other appropriate data, that can be used to determine the altitude, and more particularly the change in altitude, of the user for a particular foot strike. More particularly, the altitude data can be used to determine whether a runner was running on a flat or substantially flat stretch of ground, or was running uphill or downhill, for each foot strike. This may be beneficial in providing context for each foot strike to ensure that accurate data and instructions are communicated to the runner, as even runners with good running for will tend to heel strike when running down a substantial incline and forefoot strike when running up a substantial incline.

In one embodiment, a shoe may have one or more control elements embedded therein to adjust an element of the shoe. For example, control elements may be embedded in the sole of a shoe to adjust a stiffness, flexibility, and/or thickness of the sole in response to a signal received from a remote source. As such, a biofeedback system can be adapted to send biofeedback information measured by one or more sensors in a shoe to a remote receiver, analyze the data to determine one or more performance characteristic of the runner during a run, and send a control signal to control elements in the shoe to adjust a characteristic of the shoe to compensate for shortcomings in the runners technique and/or to assist in training the runner to run with proper form. In an alternative embodiment the analyzing and controlling steps may be carried out by a control element embedded within, or attached to, the shoe, without the need for a remote receiver.

While the discussions hereinabove relate to the use of sensors to measure an provide feedback relating to a runners form during jogging or running, in alternative embodiments the systems and methods described herein may be used to measure one or more performance characteristics related to athletic activities other than running. For example, the systems and methods described herein may be useful for training purposes in sports that require an athlete to make rapid changes of direction (e.g., soccer, football, basketball, baseball, softball, tennis, squash, badminton, volleyball, lacrosse, field hockey, ultimate Frisbee, etc), where analysis of the athlete's foot striking during a turn or "cut" may provide valuable performance information. Similarly, sports that require good jumping form when jumping (e.g., hurdling, basketball, volleyball, etc) may also benefit from devices and methods that provide accurate information relating to the position of the athlete's foot during push of and/or landing. In addition, devices that provide accurate information about the position and rotation of the feet of a user may provide valuable training information for a golfer during a swing, for a bowler during a throwing action, for a baseball pitcher during a throw, or for other athletic motions requiring a high degree of repeatability.

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

What is claimed is:

1. An apparatus for monitoring one or more athletic performance characteristics of a user, the apparatus comprising:
   a sensing unit adapted to be attachable to a shoe of a user, the sensing unit comprising:
   (i) a first sensor adapted to monitor a movement of a foot of the user while the user is in motion, the first sensor comprising a gyroscopic sensor for measuring angular velocity data for the foot of the user;
   (ii) processing means for (a) processing the angular velocity data from the first sensor to determine a processed value indicative of a first athletic performance characteristic comprising a foot strike location of a foot of the user upon striking a ground surface, and (b) comparing the processed value to a range of predetermined comparison values to determine the athletic performance characteristic relating to the processed value, the range of comparison values comprising a first range of values indicative of a heel strike, a second range of values indicative of a midfoot strike, and a third range of values indicative of a forefoot strike;
   (iii) a periodic trigger adapted to distinguish one stride from another for determining a point in time in each gait cycle before a foot strike event takes place to trigger the processing means to process angular velocity data from the first sensor to identify a maximum value and a minimum value during a window of time, wherein the point in time is triggered when, during a foot swing portion of each gait cycle, a sum of negative angular velocities, measured by the first sensor, reaches a preset level; and
   (iv) transmitting means for transmitting a data package representative of the performance characteristic to a remote receiver, the data package comprising an indication of whether a heel strike, a midfoot strike, or a forefoot strike has occurred.

2. The apparatus of claim 1, further comprising receiving means for: (i) receiving the data package transmitted from the sensing unit, and (ii) communicating information representative of the performance characteristic to the user.

3. The apparatus of claim 2, wherein the receiving means comprises at least one of a visual signal, an auditory signal, and a tactile signal.

4. The apparatus of claim 2, wherein the information is communicated to the user in substantially real-time.

5. The apparatus of claim 2, wherein the receiving means comprises at least one remote user feedback device.

6. The apparatus of claim 5, wherein the remote user feedback device is selected from the group consisting of: a watch, a detachable strap, a mobile phone, an earpiece, a hand-held feedback device, a laptop computer, a head-mounted feedback device, and a desktop personal computer.

7. The apparatus of claim 2, wherein the receiving means comprises means for controlling at least one function of a remote user feedback device.

8. The apparatus of claim 2, wherein at least one of the sensing unit and the receiving means comprises means for storing data related to the first athletic performance characteristic.

9. The apparatus of claim 1, wherein the processing means comprises a microprocessor.

10. The apparatus of claim 1, wherein the sensing unit comprises a housing unit adapted to house the first sensor, the processing means, and the transmitting means.

11. The apparatus of claim 10, wherein the housing unit is adapted to be releasably attachable to the shoe of the user.

12. The apparatus of claim 11, wherein the housing unit is adapted to be releasably attachable to at least one of a fastening portion and a heel portion of the shoe.

13. The apparatus of claim 1, further comprising means for determining at least one second athletic performance characteristic of the user.

14. The apparatus of claim 13, wherein the determination of the at least one second athletic performance characteristic is based upon an output from the first sensor.

15. The apparatus of claim 13, wherein the determination of the at least one second athletic performance characteristic is based upon an output from at least one second sensor.

16. The apparatus of claim 15, wherein the at least one second sensor is selected from the group consisting of: an accelerometer, a pressure sensor, a force sensor, a temperature sensor, a chemical sensor, a global positioning system, a piezoelectric sensor, a rotary position sensor, a gyroscopic sensor, a heart-rate sensor, and a goniometer.

17. The apparatus of claim 13, wherein the at least one second athletic performance characteristic comprises at least one of a cadence, a posture, a lean, a speed, a distance travelled, or a heart rate of the user.

18. The apparatus of claim 1, wherein the processing means performs a comparison of a localized maximum angular velocity measurement and a localized minimum angular velocity measurement during a foot strike event to determine the processed value.

19. The apparatus of claim 18, wherein the processing means divides the localized minimum angular velocity measurement during a foot strike event by the localized maximum angular velocity measurement during a foot strike event to determine the processed value.

20. The apparatus of claim 1, wherein the processing means integrates measured angular velocity data during a foot strike event to determine the processed value.

21. A method for monitoring one or more athletic performance characteristics of a user, the method comprising the steps of:
   providing a sensing unit adapted to be attachable to a shoe of a user, the sensing unit comprising:
      (i) a first sensor adapted to monitor a movement of a foot of the user while the user is in motion, the first sensor comprising a gyroscopic sensor for measuring angular velocity data for the foot of the user,
      (ii) processing means for (a) processing the angular velocity data from the first sensor to determine a processed value indicative of a first athletic performance characteristic comprising a foot strike location of a foot of the user upon striking a ground surface, and (b) comparing the processed value to a range of predetermined comparison values to determine the athletic performance characteristic relating to the processed value, the range of comparison values comprising a first range of values indicative of a heel strike, a second range of values indicative of a midfoot strike, and a third range of values indicative of a forefoot strike,
      (iii) a periodic trigger adapted to distinguish one stride from another for determining a point in time in each gait cycle before a foot strike event takes place to trigger the processing means to process angular velocity data from the first sensor to identify a maximum value and a minimum value during a window of time, wherein the point in time is triggered when, during a foot swing portion of each gait cycle, a sum of negative angular velocities, measured by the first sensor, reaches a preset level, and
      (iv) transmitting means for transmitting a data package representative of the performance characteristic to a remote receiver, the data package comprising an indication of whether a heel strike, a midfoot strike, or a forefoot strike has occurred; and
   providing receiving means for receiving the data package transmitted from the sensing unit and communicating information representative of the performance characteristic to the user.

22. The method of claim 21, wherein the information is communicated to the user in substantially real-time.

23. The apparatus of claim 1, wherein the periodic trigger comprises a second sensor.

24. The apparatus of claim 1, wherein the periodic trigger triggers at a pre-set angular velocity measurement from the first sensor.

25. The apparatus of claim 1, wherein the window of time comprises a starting point associated with initiation of the foot strike event.

26. The apparatus of claim 25, wherein the starting point comprises a pre-set angular velocity measurement.

27. The apparatus of claim 25, wherein the starting point comprises a moment before the initiation of the foot strike event.

28. The apparatus of claim 25, wherein the starting point comprises a moment of initial impact of the foot strike event.

29. The apparatus of claim 25, wherein the starting point comprises a moment of a first local maximum angular velocity measurement after an initial impact of the foot strike event.

30. The apparatus of claim 25, wherein the starting point comprises a moment of an angular velocity measurement of about zero prior to an initial impact of the foot strike event.

31. The apparatus of claim 25, wherein the window of time comprises a temporal length from the starting point to an ending point.

32. The apparatus of claim 31, wherein the ending point comprises a moment of a transition from a negative angular velocity measurement to a positive angular velocity measurement after a local minimum angular velocity measurement.

33. The apparatus of claim 31, wherein the ending point comprises a moment of a first local minimum angular velocity measurement after the foot strike event.

34. The apparatus of claim 31, wherein the temporal length comprises between about 10 msec and about 50 msec.

35. The apparatus of claim 31, wherein the temporal length comprises a period between a moment of a first local maximum angular velocity measurement after an initial impact of the foot strike event and a moment of a first local minimum angular velocity measurement.

36. The apparatus of claim 21, wherein the gyroscopic sensor is activated only when the user is running.

* * * * *